United States Patent
Van Venrooij et al.

(10) Patent No.: US 9,689,871 B2
(45) Date of Patent: Jun. 27, 2017

(54) METHOD OF DETECTING AUTO-ANTIBODIES FROM PATIENTS SUFFERING FROM RHEUMATOID ARTHRITIS, A PEPTIDE AND AN ASSAY KIT

(71) Applicant: STICHTING VOOR DE TECHNISCHE WETENSCHAPPEN, Utrecht (NL)

(72) Inventors: Waltherus Jacobus Wilhelmus Van Venrooij, Nijmegen (NL); Jan Wouter Drijfhout, Leiden (NL); Martinus Adrianus Maria Van Boekel, Nistelrode (NL); Gerardus Jozef Maria Pruijn, Beuningen (NL)

(73) Assignee: STICHTING VOOR DE TECHNISCHE WETENSCHAPPEN, Utrecht (NL)

( * ) Notice: Subject to any disclaimer, the term of this patent is extended or adjusted under 35 U.S.C. 154(b) by 362 days.

(21) Appl. No.: 14/286,878

(22) Filed: May 23, 2014

(65) Prior Publication Data

US 2014/0336069 A1  Nov. 13, 2014

Related U.S. Application Data

(60) Division of application No. 13/920,017, filed on Jun. 17, 2013, now Pat. No. 8,759,114, which is a division of application No. 13/012,739, filed on Jan. 24, 2011, now Pat. No. 8,481,332, which is a continuation of application No. 10/497,667, filed as application No. PCT/NL02/00815 on Dec. 11, 2002, now Pat. No. 7,888,133.

(30) Foreign Application Priority Data

Dec. 11, 2001  (NL) ...................... 1019540

(51) Int. Cl.
| | | |
|---|---|---|
| *G01N 33/564* | (2006.01) | |
| *C07K 7/08* | (2006.01) | |
| *C07K 14/47* | (2006.01) | |
| *C07K 7/64* | (2006.01) | |
| *C07K 7/52* | (2006.01) | |

(52) U.S. Cl.
CPC ............ *G01N 33/564* (2013.01); *C07K 7/08* (2013.01); *C07K 7/52* (2013.01); *C07K 7/64* (2013.01); *C07K 14/4713* (2013.01); *G01N 2410/00* (2013.01); *G01N 2800/102* (2013.01); *Y10S 435/973* (2013.01); *Y10S 435/975* (2013.01); *Y10S 530/806* (2013.01)

(58) Field of Classification Search
CPC ............ G01N 33/564; G01N 2410/00; G01N 2800/102; C07K 7/08; C07K 7/52; C07K 7/64; Y01S 435/973; Y01S 435/975; Y01S 530/806

See application file for complete search history.

(56) References Cited

U.S. PATENT DOCUMENTS

| | | | |
|---|---|---|---|
| 5,420,016 A * | 5/1995 | Boguslaski | C12Q 1/04 106/2 |
| 5,888,833 A | 3/1999 | Serre et al. | |
| 6,858,438 B2 | 2/2005 | Van Venrooij et al. | |
| 6,890,720 B1 | 5/2005 | Serre et al. | |
| 7,335,724 B2 | 2/2008 | Van Venrooij et al. | |
| 7,888,133 B2 | 2/2011 | Van Venrooij et al. | |
| 8,481,332 B2 * | 7/2013 | Van Venrooij | C07K 7/08 435/69.3 |
| 8,759,114 B2 * | 6/2014 | Van Venrooij | C07K 7/08 435/69.3 |

FOREIGN PATENT DOCUMENTS

| | | |
|---|---|---|
| WO | WO-98/22503 A2 | 5/1998 |
| WO | WO-99/28344 A2 | 6/1999 |
| WO | WO-99/35167 A1 | 7/1999 |
| WO | WO-01/02437 A1 | 1/2001 |
| WO | WO-01/46222 A2 | 6/2001 |
| WO | WO-01/90197 A1 | 11/2001 |

OTHER PUBLICATIONS

Harlow, E. and Lane, D., Antibodies: A Laboratory Manual (1988) Cold Spring Harbor Laboratory Press, Cold Spring Harbor, NY, pp. 23-26.*
Lederman et al. "A single amino acid substitution in a common African allele of the CD4 molecule ablates binding of the monoclonal antibody, OKT4" Mol Immunol. Nov. 1991;28(11):1171-81.*
Colman et al. Research in Immunology, 1994; 145(1): 33-36.*
De Koster et al., J. Immunol. Methods (1995) 187:177-188.
International Search Report for PCT/NL02/00815, mailed on Sep. 8, 2003, 2 pages.
Girbal-Neuhauser et al., J. Immunology (1999) 162:585-594.
Schellekens et al., Arthritis and Rheumatism (2000) 43(1):155-163.
Schellekens et al., J. Clin. Invest. (1998) 101(1):273-281.
Sonke et al., "Aminoamidase-Catalyzed Preparation and Further Transformations of Enantiopure α-Hydrogen- and αα-Disubstituted α-Amino Acids" in Stereoselective Biocatalysis (2000) pp. 23-58.

* cited by examiner

*Primary Examiner* — Gary W Counts
(74) *Attorney, Agent, or Firm* — Morrison & Foerster LLP

(57) ABSTRACT

Peptides useful in determining the presence of autoantibodies in patients suffering from rheumatoid arthritis are disclosed.

6 Claims, 2 Drawing Sheets m = 0, 1, 2; n = 0, 1, 2; V = CH$_2$, S; X = O, S, NR; Y = CH$_2$, NH; R, R$^1$, R$^2$ = H, aryl, (cyclo)alkyl m = 0, 1, 2; n = 0, 1, 2; X = O, S, NR; Y = CH, N; Z = NR$^1$, O, CH$_2$; R, R$^1$ = H, (cyclo)alkyl, aryl

METHOD OF DETECTING AUTO-ANTIBODIES FROM PATIENTS SUFFERING FROM RHEUMATOID ARTHRITIS, A PEPTIDE AND AN ASSAY KIT

CROSS-REFERENCE TO RELATED APPLICATION

This application is a divisional of U.S. Ser. No. 13/920,017 filed 17 Jun. 2013, now U.S. Pat. No. 8,759,114, which is a divisional of copending U.S. Ser. No. 13/012,739 filed 24 Jan. 2011, U.S. Pat. No. 8,481,332, which is a continuation of U.S. Ser. No. 10/497,667 having an international filing date of 11 Dec. 2002, now U.S. Pat. No. 7,888,133, issued 15 Feb. 2011, which is the national phase of PCT Application PCT/NL02/00815 having an international filing date of 11 Dec. 2002, and claims priority from Netherlands Application No. 1019540 filed 11 Dec. 2001. The contents of these documents are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 595402000211CorrectedSeqList, date recorded: Jul. 23, 2014, size: 58,234 bytes).

FIELD OF THE INVENTION

The present invention relates to a method of detecting autoantibodies from patients suffering from rheumatoid arthritis, using a peptide comprising a citrulline residue or analogue thereof.

BACKGROUND ART

Such a method is known from the international patent application PCT/NL97/00624. This publication describes the use of peptides derived from filaggrin, and which comprise citrulline or an analogue thereof for the detection of autoantibodies from patients suffering from rheumatoid arthritis. The peptides used are therefore suitable for diagnostic applications, and compared with up to then, make a more reliable detection possible. More in particular this concerns a decrease in false-positives, i.e., a higher specificity. In addition, the sensitivity is relatively high. One peptide, indicated as cfc1, was recognized by 36% of the sera from patients suffering from rheumatoid arthritis. The cyclic variant of the peptide appeared to be recognized even better (63%).

A method according to the preamble is also known from the international patent application PCT/FR00/01857. This publication describes the use of peptides derived from fibrin or fibrinogen, and which comprise citrulline or an analogue thereof for the detection of autoantibodies from patients suffering from rheumatoid arthritis.

PCT/EP98/07714 describes the use of synthetic peptides derived from (pro)filaggrin for the diagnosis of rheumatoid arthritis. This application also describes synthetic peptides derived from human vimentin, cytokeratin 1, cytokeratin 9 and other intermediary filament proteins.

However, the above-mentioned methods still only detect a limited number of all the patients suffering from rheumatoid arthritis. Therefore there is a strong need for a method by which an increased sensitivity can be achieved while maintaining a substantially equal or even improved specificity.

DISCLOSURE OF THE INVENTION

In order to achieve this objective, the present invention provides a method as mentioned in the preamble, which method is characterized in that said autoantibodies are contacted with a peptide unit comprising the motif XG, and a peptide unit comprising the motif XnonG, wherein X is a citrulline residue or an analogue thereof, G is the amino acid glycine and nonG is an amino acid other than glycine.

The experiments described below have shown that sera obtained from patients suffering from rheumatoid arthritis contain two different populations of antibodies. The one population is reactive with XG peptide units such as have been described in the above-mentioned pre-published literature. The population can in part be detected with the pre-published XG peptide units and for a still larger part when using the peptide units according to the present invention. The other population of antibodies reacts with XnonG peptide units. Until now, this population of antibodies has not yet been observed as such in the pre-published literature. As described below in more detail, the majority of sera from patients suffering from rheumatoid arthritis comprise both populations of antibodies. Consequently these sera can be detected by means of a diagnostic test comprising an XG or an XnonG peptide unit. It appears however, that a significant part of the sera from patients suffering from rheumatoid arthritis comprises only one of the two populations. Therefore, sera that comprise antibodies to the XnonG peptide unit only are not or only for a very small part detected with the diagnostic tests as described in the above-mentioned published literature. A large part of these sera can now be detected if the diagnostic test comprises a XnonG peptide unit. An improved diagnostic method according to the present invention therefore comprises at least one XG and one XnonG peptide. Thus the diagnostic test according to the invention may be 20% more sensitive than a test according to the published literature.

Particularly good results were obtained when the peptide unit with the XnonG motif comprised a part not derived from natural proteins such as human (pro)filaggrin, fibrin, or fibrinogen as well as the related proteins vimentin, and cytokeratin 1 and cytokeratin 9 or other related intermediary filament proteins.

Surprisingly it was shown, that when combining such XnonG peptides not derived from natural proteins with XG peptides according to the invention, a further improved diagnostic method was obtained. More in particular, the use of such a combination of peptide units in the method according to the present invention provides a diagnostic method of a very great sensitivity, while maintaining an excellent specificity. This is all the more surprising, since the above-mentioned published literature is still based on the idea that autoantibodies from patients with RA reacted especially well with peptides derived from naturally-occurring protein such a (pro)filaggrin, fibrin, fibrinogen, vimentine, cytokeratin 1 or cytokeratin 9. PCT/EP98/07714, for example, describes a filaggrin-derived XnonG peptide (IPG1249). It is cross-reactive with 3.3% of the sera from SLE patients and has a homology of 82% with filaggrin.

Good results are obtained when the peptide unit with the XnonG motif comprises a tripeptide, in which the central amino acid is citrulline or an analogue thereof, and that a selection is preferably made from XXK, XXY, KXI, MXR, RXY, WXK, MXH, VXK, NXR, WXS, RXW, YXM, IXX, XXF, RXH, TXV, PXH, AXF, FXR, YXF, LXM, LXY, YXP, HXS and PXW.

Preferably nonG is an amino acid selected from H, I, W, S, R, K, Y, M, F, V, P, Cit or an analogue thereof. As shown in the experiments below, such XnonG peptide units are very effective.

The peptide unit comprising the XG motif, may or may not be derived from (pro)filaggrin, fibrin, fibrinogen, vimentin, cytokeratin 1 or cytokeratin 9, and effectively the cfc1 known from PCT/NL97/00624.

In this context the term amino acid includes both natural and non-natural amino acids, as well as amino acids having a D-configuration or L-configuration.

In the present application a non-natural amino acid is understood to be an amino acid of the kind occurring in an retro-inverso peptide, retro-peptide, a peptide wherein the side chain is located on the amide nitrogen atom of the peptide linkage, and a peptide wherein a CO of the peptide linkage is replaced by 2, 3 or preferably a single —$CH_2$— group (pseudo-peptide).

Amino acids may also be modified. For example, carboxylic acid groups may be esterified or may be converted to an amide, and an aminogroup may be alkylated, for example methylated. Alternatively, functional groups on the peptide may be provided with a protective group or a label (for example a fluorescent or radioactive label). Aminogroups and carboxylic acid groups in the peptides may be present in the form of a salt formed by using an acid or a base. If synthetic peptides are used, it is very simple to make all kinds of variants falling within the scope of the invention that can be used. For example, aromatic side groups such as from phenylalanine and tyrosine may be halogenated with one or more halogen atoms. Peptidomimetic and organomimetic embodiments also fall within the scope of the invention and their application in the method according to the invention. Instead of a Cit residue it is also possible to use an analogue thereof, such as those represented in FIG. 1 in the form of the amino acid. Such analogues and their preparation are known to the person skilled in the art. For example, Sonke, et al., in *Stereoselective Biocatalysis* (2000), pp. 23-58, and Greene: *Protective Groups in Organic Synthesis* (Wiley, New York 1999. In accordance with a favourable embodiment, the side chains of the citrulline analogues have the formula (I):

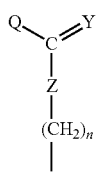

(I)

wherein
Q=$NH_2$, $CH_3$, $NHCH_3$ or $N(CH_3)_2$;
Y=O, NH, or $NCH_3$;
Z=O, NH or $CH_2$; and
n=2, 3 or 4;
on the condition that if Q=$NH_2$ and Z=NH, Y is not NH.

In this context, a peptide unit is understood to be a peptide that is at least 7 amino acids long. Peptide units may have one or more side chains. Also, peptide units or terminal ends of the peptide unit may be acetylated, glycosylated, alkylated, or phosphorylated independently of each other.

A peptide unit in this context is indicated as not derived from (pro)filaggrin, fibrin, fibrinogen, vimentin, cytokeratin 1 or cytokeratin 9 and other intermediary filament proteins if the homology (the similarity of the amino acid sequence) to these proteins is less than 80%, more preferably less than 75% such as less than 70% or 65%, and most preferably less than 60%, such as less than 55% or 50%. The peptide units shown in Table 5, which are not derived from (pro)filaggrin, fibrin, fibrinogen, vimentin, cytokeratin 1 and cytokeratin 9, have a homology between 15 and 45%. On examination of the homology arginine, citrulline and analogues of citrulline are considered to be equivalent (identical).

The peptide units comprising XG and XnonG may or may not part of the same molecule. This will be entered into later on. For carrying out a detection assay, the peptide units may be bound to a carrier and optionally provided with a label. The complex may be detected in any manner well-known to the ordinary person skilled in the art. The complex may be detected indirectly, for example in the case of a competition assay, in which the complex itself is not labelled. The reaction with the two peptide units may take place simultaneously or successively and in the same container (such as a well of a microtitre plate) or in different containers.

MODES OF CARRYING OUT THE INVENTION

Figure 1A:
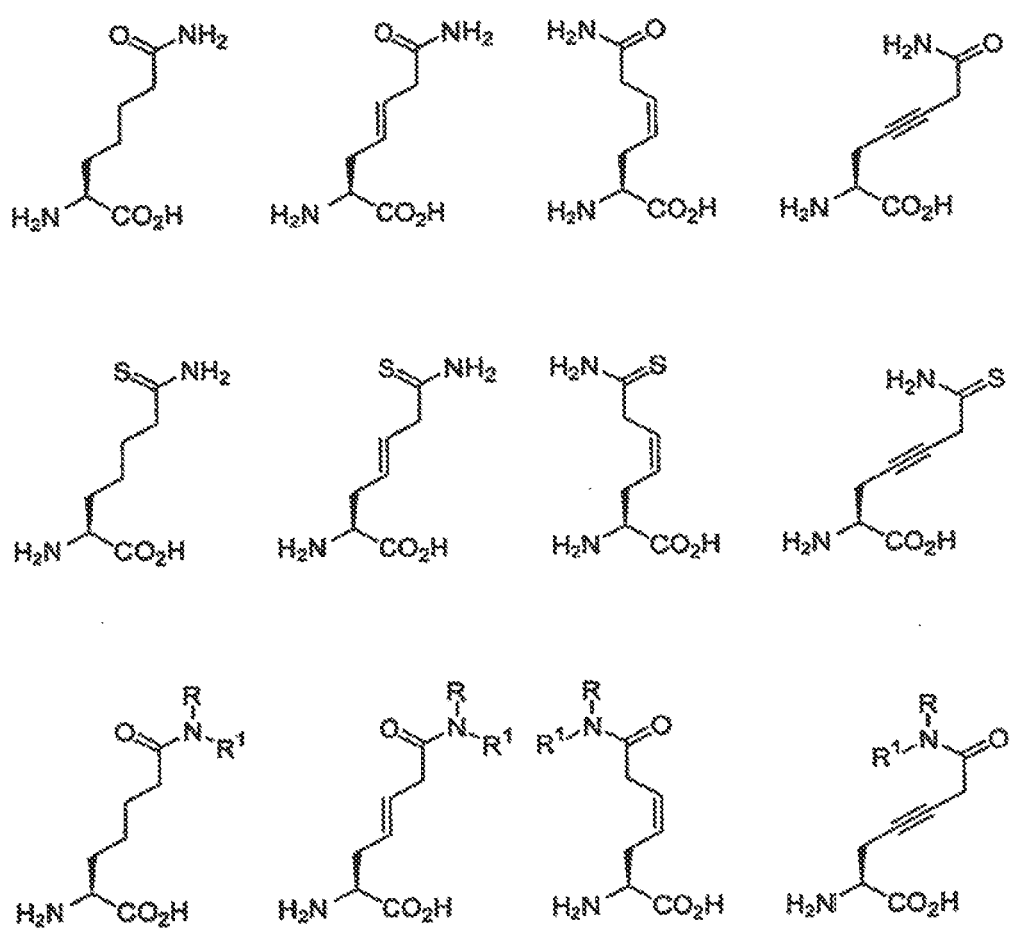
FIGS. 1a and 1b show structures of various citrulline analogues.
Figure 1B:
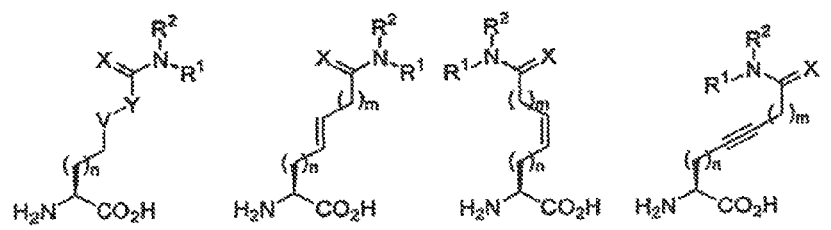
Figure 1B:
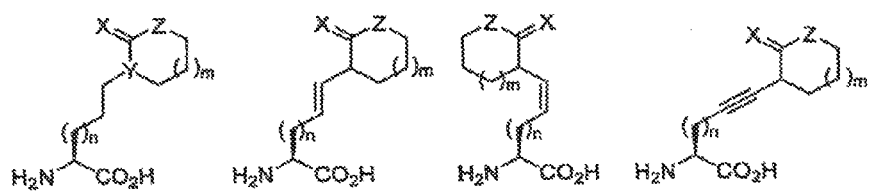

This application is not intended as an educational publication on how to become a person skilled in the art. It is therefore limited to providing sufficient information to enable the ordinary person skilled in the art to understand the invention, and to work it, and to understand the scope of protection.

Preferably the peptide units are recognized by at least 2 of 100 random sera from recognized RA patients. Obviously it is preferred to use peptide units that are recognized by a considerably higher percentage, preferably at least 30%. The number of peptide units in a method according to the invention is preferably 2 or greater than 2.

Preferably the invention relates to a method as mentioned above, wherein the peptide unit with the XG motif and peptide unit with the XnonG motif are recognized together by at least 10% of the series of sera from patients. Of course, combinations of peptide units resulting in higher sensitivities are preferred. With some combinations of peptide units as described in this document, diagnostic tests can be carried out with sensitivities of 40, 60, 70, 80 or even 85 and more than 90%.

It has been shown that the sensitivity of the detection can be further increased if at least one of the peptide units is a cyclic peptide unit.

The peptide unit with XG motif and the peptide unit with XnonG motif are preferably part of a multipeptide. In the context of the present invention, a multipeptide is a molecule comprised of at least two antigenic peptide units, i.e., combinations of peptide units that may or may not be linked by a covalent bond. Such multipeptides may be comprised of linear, branched, cyclic peptide units or a combination of these. Multipeptides may be comprised both of peptide units having the same amino acid sequence, and of peptide units having different amino acid sequences. A multipeptide according to the invention comprises at least 7, preferably at least 10 amino acids, i.e., the peptide units may overlap. It goes without saying that the XG and XnonG motif can not overlap.

The invention also relates to a XnonG peptide unit, very useful for the method according to the present invention, comprising a sequence with the formula (II):

(A1-A2-A3-A4-A5)-Cit-(A6)-(A7-A8-A9-A10-A11)  (II)

wherein
A1-A2-A3-A4-A5 is an amino acid sequence selected from

| | |
|---|---|
| RHGRQ | (SEQ ID NO: 13) |
| IRCitYK | (SEQ ID NO: 14) |
| HGRQCit | (SEQ ID NO: 15) |
| GRQCitCit | (SEQ ID NO: 16) |
| FQMCitH | (SEQ ID NO: 17) |
| CitWRGM | (SEQ ID NO: 18) |
| ARFQM | (SEQ ID NO: 19) |
| QCitYKW | (SEQ ID NO: 20) |
| KPYTV | (SEQ ID NO: 21) |
| RNLRL | (SEQ ID NO: 22) |
| RRRCitY | (SEQ ID NO: 23) |
| RFKSN | (SEQ ID NO: 24) |
| RGKSN | (SEQ ID NO: 25) |
| RWVSQ | (SEQ ID NO: 26) |
| MKPRY | (SEQ ID NO: 27) |
| KSFVW | (SEQ ID NO: 28) |
| YSFVW | (SEQ ID NO: 29) |
| FQMRH | (SEQ ID NO: 30) |
| RNMNR | (SEQ ID NO: 31) |
| RMGRP | (SEQ ID NO: 32) | and homologous sequences thereof;
A7 an amino acid other than glycine;
A7-A8-A9-A10-A11 an amino acid sequence selected from

| | |
|---|---|
| KYIIY | (SEQ ID NO: 33) |
| TNRKF | (SEQ ID NO: 34) |
| KWCitKI | (SEQ ID NO: 35) |
| CitRAVI | (SEQ ID NO: 36) |
| RCitGHS | (SEQ ID NO: 37) |
| CitGRSR | (SEQ ID NO: 38) |
| CitYIIY | (SEQ ID NO: 39) |
| CitRLIR | (SEQ ID NO: 40) |
| IERKR | (SEQ ID NO: 41) |
| FMRKP | (SEQ ID NO: 42) |
| FMRRP | (SEQ ID NO: 43) |
| ERNHA | (SEQ ID NO: 44) |
| AVITA | (SEQ ID NO: 45) |
| TPNRW | (SEQ ID NO: 46) |
| TYNRW | (SEQ ID NO: 47) |
| RTPTR | (SEQ ID NO: 48) |
| RIVVV | (SEQ ID NO: 49) |
| HARPR | (SEQ ID NO: 50) |
| RGMCitR | (SEQ ID NO: 51) |
| IRFPV | (SEQ ID NO: 52) | and homologous sequences thereof;
as well as functional analogues of the peptide with the formula (II).

The invention also relates to a XnonG peptide unit, very useful for the method according to the present invention, comprising a sequence with the formula (III):

(B1-B2-B3-B4-B5-B6)-Cit-(B7)-(B8-B9-B10-B11)  (III)

wherein
B1-B2-B3-B4-B5-B6 is an amino acid sequence selected from

| | |
|---|---|
| INCitRAS | (SEQ ID NO: 53) |
| ICitKRLY | (SEQ ID NO: 54) |
| KCitCitYNI | (SEQ ID NO: 55) |
| RLYFICit | (SEQ ID NO: 56) |
| IRQGAR | (SEQ ID NO: 57) |
| CitERCitVQ | (SEQ ID NO: 58) |
| CitHQRIT | (SEQ ID NO: 59) |
| RICitRVCit | (SEQ ID NO: 60) |
| GRNQRY | (SEQ ID NO: 61) |
| RCitRQHP | (SEQ ID NO: 62) |
| CitCitRCitVA | (SEQ ID NO: 63) |
| RPKQHV | (SEQ ID NO: 64) |
| RKCitGCitR | (SEQ ID NO: 65) |
| RCitCitRNT | (SEQ ID NO: 66) |
| RCitQCitFT | (SEQ ID NO: 67) |
| QLVYLQ | (SEQ ID NO: 68) |
| QYNRFK | (SEQ ID NO: 69) |
| CitLRHIR | (SEQ ID NO: 70) |
| PRCitCitCitK | (SEQ ID NO: 71) |
| RCitQVRY | (SEQ ID NO: 72) |
| GRCitHAH | (SEQ ID NO: 73) |
| ARHVIR | (SEQ ID NO: 74) |

-continued

| | |
|---|---|
| RCitGHMF | (SEQ ID NO: 75) |
| GRNIRV | (SEQ ID NO: 76) |
| QIFYLCit | (SEQ ID NO: 77) |
| RQGPIA | (SEQ ID NO: 78) |
| GVYLVR | (SEQ ID NO: 79) |
| NCitCitRRV | (SEQ ID NO: 80) |
| KCitRLCitY | (SEQ ID NO: 81) |
| GRRCitCitL | (SEQ ID NO: 82) |
| RMPHCitH | (SEQ ID NO: 83) | and homologous sequences thereof;
B7 is an amino acid other than glycine;
B8-B9-B10-B11 an amino acid sequence selected from

| | |
|---|---|
| CitHRR | (SEQ ID NO: 84) |
| CitIRR | (SEQ ID NO: 85) |
| FRRN | (SEQ ID NO: 86) |
| AQTT | (SEQ ID NO: 87) |
| GYPK | (SEQ ID NO: 88) |
| RPPQ | (SEQ ID NO: 89) |
| GCitRK | (SEQ ID NO: 90) |
| PIPR | (SEQ ID NO: 91) |
| YTIH | (SEQ ID NO: 92) |
| RIKA | (SEQ ID NO: 93) |
| CitRVR | (SEQ ID NO: 94) |
| TRRP | (SEQ ID NO: 95) |
| TIRP | (SEQ ID NO: 96) |
| IKCitR | (SEQ ID NO: 97) |
| RNVV | (SEQ ID NO: 98) |
| CitRRY | (SEQ ID NO: 99) |
| CitRPR | (SEQ ID NO: 100) |
| TRCitCit | (SEQ ID NO: 101) |
| CitCitGR | (SEQ ID NO: 102) |
| LCitRCit | (SEQ ID NO: 103) |
| RVRCit | (SEQ ID NO: 104) |
| VPRT | (SEQ ID NO: 105) |
| YCitFR | (SEQ ID NO: 106) |
| ARCitCit | (SEQ ID NO: 107) |
| RQCitR | (SEQ ID NO: 108) |
| HIRR | (SEQ ID NO: 109) |
| CitMMR | (SEQ ID NO: 110) |
| CitRICit | (SEQ ID NO: 111) |
| VRKS | (SEQ ID NO: 112) |

-continued

| | |
|---|---|
| PCitCitR | (SEQ ID NO: 113) |
| CitRRK | (SEQ ID NO: 114) | and homologous sequences thereof;
as well as functional analogues of the peptide with the formula (III).

The term "homologous sequence", as used in connection with A1-A2-A3-A4-A5, A7-A8-A9-A10-A11, B1-B2-B3-B4-B5-B6 and B8-B9-B10-B11, means that at most two amino acids of each amino acid sequence may be replaced by as many other amino acids (including citrulline and/or an analogue thereof), at most two amino acids (including or an analogue thereof) may be introduced and at most two amino acids may be absent.

The term 'analogue' as used in connection with the peptide of the formula (II) or (III) means that optionally
- one or more amino acids may have the D-configuration,
- one or more side chains (other than that of citrulline or an analogue thereof) or terminal ends of the peptide may be acetylated, glycosylated, alkylated, or phosphorylated independently of each other, and
- one or more amino acids may be replaced by non-natural amino acids.

A6 and B7 (independent of each other) are preferably selected from Cit, H, I, K, R, S, W, Y, M, F, V and P.

Specific preferred peptides to be used in the method according to the invention are characterized in that they comprise at least one peptide sequence selected from

| | |
|---|---|
| R H G R Q Cit Cit K Y I I Y | (SEQ ID NO: 115) |
| I R Cit Y K Cit I T N R K F | (SEQ ID NO: 116) |
| R H G R Q Cit Cit Cit Y I I Y | (SEQ ID NO: 117) |
| A R F Q M Cit H Cit R L I R | (SEQ ID NO: 118) |
| Q Cit Y K W Cit K I E R K R | (SEQ ID NO: 119) |
| K P Y T V Cit K F M R K P | (SEQ ID NO: 120) |
| K P Y T V Cit K F M R R P | (SEQ ID NO: 121) |
| R N L R L Cit R E R N H A | (SEQ ID NO: 122) |
| R R R Cit Y Cit R A V I T A | (SEQ ID NO: 123) |
| R F K S N Cit R T P N R W | (SEQ ID NO: 124) |
| R G K S N Cit R T Y N R W | (SEQ ID NO: 125) |
| R F K S N Cit R T Y N R W | (SEQ ID NO: 126) |
| R G K S N Cit R T P N R W | (SEQ ID NO: 127) |
| R W V S Q Cit R R T P T R | (SEQ ID NO: 128) |

-continued

MKPRY Cit R RIVVV  (SEQ ID NO: 129)

KSFVW Cit S HARPR  (SEQ ID NO: 130)

YSFVW Cit S HARPR  (SEQ ID NO: 131)

RNMNR Cit WRGM Cit R,  (SEQ ID NO: 132)
and

RMGRP Cit WIRFPV  (SEQ ID NO: 133)

as well as

INCitRASCitKCitHRR  (SEQ ID NO: 134)

ICitKRLYCitMCitIRR  (SEQ ID NO: 135)

KCitCitYNICitCitFRRN  (SEQ ID NO: 136)

RLYFICitCitRAQTT  (SEQ ID NO: 137)

IRQGARCitRGYPK  (SEQ ID NO: 138)

CitERCitVQCitRRPPQ  (SEQ ID NO: 139)

CitHQRIICitVGCitRK  (SEQ ID NO: 140)

RICitRVCitCitTPIPR  (SEQ ID NO: 141)

GRNQRYCitLYTIH  (SEQ ID NO: 142)

RCitRQHPCitHRIKA  (SEQ ID NO: 143)

CitCitRCitVACitFCitRVR  (SEQ ID NO: 144)

RPKQHVCitHTRRP  (SEQ ID NO: 145)

RKCitGCitRCitCitTIRP  (SEQ ID NO: 146)

RCitCitRNTCitHIKCitR  (SEQ ID NO: 147)

RCitQCitFTCitCitRNVV  (SEQ ID NO: 148)

QLVYLQCitCitCitRRY  (SEQ ID NO: 149)

QYNRFKCitCitCitRPR  (SEQ ID NO: 150)

CitLRHIRCitQTRCitCit  (SEQ ID NO: 151)

PRCitCitCitKCitRCitCitGR  (SEQ ID NO: 152)

RCitQVRYCitCitLCitRCit  (SEQ ID NO: 153)

GRCitHAHCitPRVRCit  (SEQ ID NO: 154)

ARHVIRCitCitVPRT  (SEQ ID NO: 155)

RCitGHMFCitVYCitFR  (SEQ ID NO: 156)

GRNIRVCitCitARCitCit  (SEQ ID NO: 157)

QIFYLCitCitHRQCitR  (SEQ ID NO: 158)

RQGPIACitLHIRR  (SEQ ID NO: 159)

GVYLVRCitLCitMMR  (SEQ ID NO: 160)

NCitCitRRVCitMCitRICit  (SEQ ID NO: 161)

KCitRLCitYCitPVRKS  (SEQ ID NO: 162)

GRRCitCitLCitRPCitCitR  (SEQ ID NO: 163)

RMPHCitHCitSCitRRK  (SEQ ID NO: 164)

or an analogue thereof.

Suitable XG peptides to be used in the method according to the invention preferably comprise the sequence with the formula (IV)

(C1-C2)-(C3-C4-C5)-X-G-C6-(C7-C8-C9-C10)    (IV)

wherein

C1-C2 is HQ, GF, EG or GV;

C3-C4-C5 represents 3 amino acids of which at least 1, and preferably 2 independently of each other are basic, aromatic or V;

C6 is equal to a basic or aromatic amino acid, or equal to A, G, E, P, V, S or Cit or analogue thereof; and C7-C8-C9-C10 is

SRAA,  (SEQ ID NO: 208)

SCitAA,  (SEQ ID NO: 209)

RPLD,  (SEQ ID NO: 210)

RVVE  (SEQ ID NO: 211)
or

PGLD;  (SEQ ID NO: 212)

as well as analogues of the peptide with the formula (IV).

The term 'analogue' as used in connection with the peptide of the formula (IV) means that optionally
one or more amino acids may have the D-configuration, one or more side chains (other than that of citrulline or an analogue thereof) or terminal ends of the peptide independently of each other may be acetylated, glycosylated, alkylated, or phosphorylated; and
one or more amino acids may be replaced by non-natural amino acids.

Specific examples of XG peptides suitable to be used in the method according to the invention comprise a sequence selected from (SEQ ID NO: 165)
H Q R K W Cit G A S R A A (SEQ ID NO: 166)
H Q H W R Cit G A S R A A (SEQ ID NO: 167)
H Q F R F Cit G Cit S R A A (SEQ ID NO: 168)
H Q E R R Cit G E S R A A (SEQ ID NO: 169)
H Q K W R Cit G F S R A A (SEQ ID NO: 170)
H Q R W K Cit G G S R A A (SEQ ID NO: 171)
H Q R R T Cit G G S R A A (SEQ ID NO: 172)
H Q R R G Cit G G S R A A (SEQ ID NO: 173)
H Q Cit F R Cit G H S R A A (SEQ ID NO: 174)
G F F S A Cit G H R P L D (SEQ ID NO: 175)
H Q E R G Cit G K S R A A (SEQ ID NO: 176)
H Q E K R Cit G K S R A A (SEQ ID NO: 177)
H Q R W L Cit G K S R A A (SEQ ID NO: 178)
H Q K R N Cit G K S R A A (SEQ ID NO: 179)
E G G G V Cit G P R V V E (SEQ ID NO: 180)
H Q W R H Cit G R S Cit A A (SEQ ID NO: 181)
H Q K W N Cit G R S R A A (SEQ ID NO: 182)
H Q K F W Cit G R S R A A (SEQ ID NO: 183)
H Q K Cit K Cit G R S R A A (SEQ ID NO: 184)
H Q K W R Cit G R S Cit A A (SEQ ID NO: 185)
H Q A W R Cit G R S Cit A A (SEQ ID NO: 186)
H Q N Q W Cit G R S R A A (SEQ ID NO: 187)
H Q N S K Cit G R S R A A (SEQ ID NO: 188)
H Q K R R Cit G R S R A A (SEQ ID NO: 189)
H Q K R F Cit G R S R A A (SEQ ID NO: 190)
H Q K R Y Cit G R S R A A -continued (SEQ ID NO: 191)
H Q K R H Cit G R S R A A (SEQ ID NO: 192)
H Q E R A Cit G S S R A A (SEQ ID NO: 193)
H Q E K M Cit G V S R A A (SEQ ID NO: 194)
H Q K R G Cit G W S R A A (SEQ ID NO: 195)
H Q R R V Cit G W S R A A (SEQ ID NO: 196)
H Q W N R Cit G W S R A A (SEQ ID NO: 197)
H Q Q R M Cit G W S R A A (SEQ ID NO: 198)
H Q S H R Cit G W S R A A (SEQ ID NO: 199)
H Q F R F Cit G W S R A A (SEQ ID NO: 200)
H Q K R R Cit G W S R A A (SEQ ID NO: 201)
G V K G H Cit G Y P G L D or an analogue thereof.

The peptides according to the invention are preferably cyclic peptides of which the ring comprises at least 10 amino acids, and more preferably at least 11 amino acids. The person skilled in the art is acquainted with various methods for the preparation of cyclic peptides and a further explanation is not required.

According to a most preferred method of the invention, an XG peptide is used in combination with at least one XnonG peptide, wherein the XG peptide is selected from the group comprised of:

(SEQ ID NO: 1)
0002-27 H Q K R G Cit G W S R A A (SEQ ID NO: 2)
0002-29 H Q R R V Cit G W S R A A (SEQ ID NO: 3)
0002-31 H Q R R T Cit G G S R A A (SEQ ID NO: 4)
0002-32 H Q R K W Cit G A S R A A (SEQ ID NO: 5)
0002-36 H Q F R F Cit G Cit S R A A (SEQ ID NO: 6)
0002-37 H Q K W R Cit G R S Cit A A (SEQ ID NO: 7)
0002-63 H Q F R F Cit G W S R A A and the XnonG peptide is chosen from the group comprised of:

(SEQ ID NO: 8)
0107-32 K P Y T V Cit K F M R R P (SEQ ID NO: 9)
0107-35 A R F Q M Cit H Cit R L I R

-continued

```
                                                   (SEQ ID NO: 10)
    0107-45  Y S F V W Cit S H A R P R (SEQ ID NO: 11)
    0113-30  A R F Q M R H Cit R L I R (SEQ ID NO: 12)
    0218-36  R N L R L Cit R E R N H A
```

Depending on the desired specificity and sensitivity of the diagnostic test and the respective population of rheumatoid arthritis sera under examination, a preferred combination of XG and XnonG peptide units is selected from the group comprised of:

0002-27 and 0107-32; 0002-27 and 0107-35; 0002-27 and 0107-45;

0002-27 and 0113-30; 0002-27 and 0218-36; 0002-29 and 0107-32; 0002-29 and 0107-35; 0002-29 and 0107-45; 0002-29 and 0113-30; 0002-29 and 0218-36; 0002-31 and 0107-32; 0002-31 and 0107-35; 0002-31 and 0107-45; 0002-31 and 0113-30; 0002-31 and 0218-36; 0002-32 and 0107-32; 0002-32 and 0107-35; 0002-32 and 0107-45; 0002-32 and 0113-30; 0002-32 and 0218-36; 0002-36 and 0107-32; 0002-36 and 0107-35; 0002-36 and 0107-45; 0002-36 and 0113-30; 0002-36 and 0218-36; 0002-37 and 0107-32; 0002-37 and 0107-35; 0002-37 and 0107-45; 0002-37 and 0113-30; 0002-37 and 0218-36; 0002-63 and 0107-32; 0002-63 and 0107-35; 0002-63 and 0107-45; 0002-63 and 0113-30; 0002-63 and 0218-36.

The above-mentioned combinations were shown to produce an average again in sensitivity of 6%, bringing the total sensitivity of such a combination test of an XG and a XnonG peptide to 75 to 78%.

The results described in the examples below further showed that the various peptide units also detected different cohorts of sera. An additional gain in sensitivity was achieved by adding a third peptide unit or even a fourth or more peptide units. Depending on the combination of peptide units selected from the above-mentioned groups, a diagnostic test according to the invention allowed sensitivities of 88-92% to be achieved.

The invention also relates to a multipeptide, characterized in that it is a linear or branched multipeptide, comprising at least two linear or cyclic peptide sequences selected independently of each other from a peptide unit selected from peptide units with the formula (II) and (III) and analogues thereof;

a peptide unit with the formula (IV) and analogues thereof.

Such a multipeptide is very suitable for use in the method according to the invention. It makes it possible to carry out the method more simply and more reliably since peptides are used in the same known ratio, and extra operations during the assay or during the preliminary work (e.g., coating a microtitre plate with multipeptide) is avoided.

The invention further relates to a diagnostic kit for determining the presence of autoantibodies from patients suffering from rheumatoid arthritis, wherein the diagnostic kit comprises a peptide or a multipeptide according to the invention, or a mixture thereof, together with at least one further reagent.

The invention also relates to a peptide or an antibody of an immunotoxin molecule as described above, or a composition thereof for use as a pharmaceutical composition.

The present invention further relates to a peptide or an antibody of an immunotoxin molecule as described above or a composition thereof for preparing a pharmaceutical composition or a diagnostic agent for rheumatoid arthritis.

The present invention also relates to the application of a peptide or a composition thereof as described above for preparing a pharmaceutical composition for the treatment of autoimmune diseases by increasing the size of antigen immune complexes, which improves the clarification of the immune complexes formed.

The present invention therefore also relates to a method for the treatment of rheumatoid arthritis by introducing into the body of a patient requiring such treatment, at least one peptide according to the invention.

The invention further relates to a method for the selection of a peptide suitable for the diagnosis of RA, wherein a peptide library is screened with antibodies obtained from patients with RA and wherein the peptide library is selected from a group comprised of:

```
                                                   (SEQ ID NO: 202)
    Lib (1):  H Q E X X Cit X X S R A A
```

Wherein X=any amino acid except cysteine and tryptophane

```
                                               (SEQ ID NOS: 203-204)
    Lib (2):  H Q X X X Cit G X S R/Cit A A
```

Wherein X=any amino acid except cysteine but including Citrulline

```
                                               (SEQ ID NOS: 205-206)
    Lib (3):  H Q E X X Cit X X S R/Cit A A
```

Wherein X=any amino acid except cysteine but including Citrulline

```
                                                   (SEQ ID NO: 207)
    Lib (4):  X X X X X X Cit X X X X X
```

Wherein X=any amino acid except cysteine but including citrulline or equivalents thereof.

Finally, the invention relates to a peptide that can be obtained with the aid of the afore-mentioned method to be used in a diagnostic assay.

The terms "a pharmaceutical composition for the treatment" or "a drug for the treatment" or "the use of proteins for the preparation of a drug for the treatment" relate to a composition comprising a peptide as described above or an antibody binding specifically to the peptide and a pharmaceutically acceptable carrier or excipient (the two terms are interchangeable) for the treatment of diseases as described above. Suitable carriers or excipients with which the ordinary person skilled in the art is familiar are saline, Ringer's solution, dextrose solution, Hank's solution, oils, ethyl oleate, 5% dextrose in saline, substances improving isotonicity and chemical stability, buffers and preservatives. Other suitable carriers include any carrier that does not itself induce the production of antibodies harmful to the individual receiving the composition, such as proteins, polysaccharides, polylactic acids, polyglycol acids, polymeric amino acids and amino acid polymers. The "drug" may be administered in any manner known to the ordinary person skilled in the art.

The peptides according to the invention may be labelled (radioactive, fluorescent or otherwise, as well known in the art) or may be provided with a carrier. In this form also such peptides fall within the scope of the invention. For example, a peptide may be coupled to a carrier protein, such as Keyhole Limpet Haemocyanin or bovine serum albumin. Also, the peptide according to the invention may be non-covalently or covalently coupled to a solid carrier, such as a microsphere (gold, polystyrene, etc.), slides, chips, or a wall of a reactor vessel or of a well of a microtitre plate. The peptide may be labelled with a direct or an indirect label. Examples include biotin, fluorescein and an enzyme, such as horseradish peroxidase. All this is generally known to the ordinary person skilled in the art and requires no further explanation.

EXAMPLES

Example 1: Peptide Synthesis

Citrullinated peptides were synthesised as described by De Koster, H. S., et al. (*J. Immunol. Methods*, 187, pp. 177-188, (1995)). Beads were used to which the peptide molecules were attached via an amide bond so that after the removal of protective groups, peptide molecules were still attached to the bead. For the synthesis of peptides an automated multiple peptide synthesiser was used (Abimed AMS422, Abimed, Langenfeld, Germany). The incorporated amino acids and the peptide linker 6-aminohexane acid were protected by a Fmoc-group, and to facilitate coupling, the protected amino acids were activated with PyBOP and N-methylmorpholine. Where necessary, the side chains were protected with groups protecting acid-sensitive side chains. The beads used had a diameter of approximately 100 µm and comprised approximately 100 pmol peptide each. It is estimated that approximately 0.5% of this amount is bound to the outside and is in principle accessible to antibodies.

For the synthesis in larger quantities, beads were used that were provided with an acid-sensitive linker. The chemistry of peptide synthesis was largely comparable with the one already described above. The peptides were split off with trifluoroacetic acid and isolated by means of ether precipitation, all in accordance with methods well-known in the art and for which the ordinary person skilled in the art requires no further explanation. It is of course also possible to acquire peptides with a desired sequence commercially. The purity and identity of the individual peptides were checked by means of analytical RP-HPLC and time-of-flight mass spectrometry (MALDI-TOF).

With the aid of the above method 4 peptide libraries were created, each comprising a large number ($8\times10^6$) citrullinated peptides. The formulas below show the amino acid sequence of the peptides in each library:

(SEQ ID NO: 202)
Lib (1): H Q E X X Cit X X S R A A

Wherein X=any amino acid except cysteine and tryptophane (SEQ ID NOS: 203-204)
Lib (2): H Q X X X Cit G X S R/Cit A A Wherein X=any amino acid except cysteine but including Citrulline (SEQ ID NOS: 205-206)
Lib (3): H Q E X X Cit X S R/Cit A A Wherein X=any amino acid except cysteine but including Citrulline (SEQ ID NO: 207)
Lib (4): X X X X X X Cit X X X X X Wherein X=any amino acid except cysteine but including Citrulline.

These libraries were screened in accordance with the method described below using sera from patients suffering from rheumatoid arthritis.

Example 2: Reaction of the Bead-Coupled Peptides with Sera from Patients Suffering from Rheumatoid Arthritis (RA)

With the aid of Protein A-Sepharose, IgG was isolated from serum from patients clinically diagnosed to be suffering from RA. The beads were incubated with a solution comprising i) total serum from the patient, or ii) IgG from a patient conjugated to a reporter enzyme (alkaline phosphatase labelling kit; Roche/Boehringer, Mannheim, Germany). For serum (i) a second incubation was carried out with an alkaline phosphatase conjugated anti-human IgG antibody (Dako D0336; Dako Immunoglobulins, Glostrup, Denmark). After each incubation the beads were thoroughly washed with Tris-HCl buffer pH 8.9 (50 mM Tris pH 8.9, 150 mM NaCl, 0.5% Tween® 20).

The beads with peptides that had bound the most human IgG (after dying with a substrate of alkaline phosphatase that is converted into an insoluble coloured product, these become the most intensely coloured beads) were selected with the aid of a microscope.

Example 3: ELISA

The most interesting peptides were synthesised in a slightly larger quantity to form a linear and a cyclic variant, and in most cases in a citrulline and arginine (=control) variant. These peptides were tested for reactivity with a series of sera from RA patients. The peptides were coated to ELISA plates and incubated with sera from RA patients. Each serum was tested in duplicate. Sera from healthy persons were used as negative control.

Example 4: The Family of XG Peptides

By using sera that gave a positive reaction with cfc1 (see PCT/NL97/00624, which is herewith included by way of reference) peptides with glycine were found on position +1 (i.e., C-terminal) in relation to the citrulline residue. Replacing G on +1 by, for example, A (alanine) reduces the reactivity by 65%. In certain peptides, the E (glutamic acid) on position −3 is preferably not replaced by A (47% loss of activity). Similarly, the Q (glutamine) on −4, the H (histidine) on −5 and the S (serine) on +3 often appeared to be advantageous.

Thus a number of peptide sequences with the combination —XG— were selected, all of which reacted with RA sera. Specific examples of preferred members of this XG family are

TABLE 1

| Family of XG peptides: | |
|---|---|
| H Q R K W Cit G A S R A A (SEQ ID NO: 165) | (0002-32) |
| H Q H W R Cit G A S R A A (SEQ ID NO: 166) | (0002-42) |
| H Q F R F Cit G Cit S R A A (SEQ ID NO: 167) | (0002-36) |
| H Q E R R Cit G E S R A A (SEQ ID NO: 168) | (020699-2) |
| H Q K W R Cit G F S R A A (SEQ ID NO: 169) | (0102-74) |
| H Q R W K Cit G G S R A A (SEQ ID NO: 170) | (0002-28) |
| H Q R R T Cit G G S R A A (SEQ ID NO: 171) | (0002-31) |
| H Q R R G Cit G G S R A A (SEQ ID NO: 172) | (0002-33) |
| H Q Cit F R Cit G H S R A A (SEQ ID NO: 173) | (0002-43) |
| G F F S A Cit G H R P L D (SEQ ID NO: 174) | (0101-7) |
| H Q E R G Cit G K S R A A (SEQ ID NO: 175) | (020699-1) |
| H Q E K R Cit G K S R A A (SEQ ID NO: 176) | (020699-4) |
| H Q R W L Cit G K S R A A (SEQ ID NO: 177) | (0002-30) |
| H Q K R N Cit G K S R A A (SEQ ID NO: 178) | (0002-38) |
| E G G G V Cit G P R V V E (SEQ ID NO: 179) | (0101-5) |
| H Q W R H Cit G R S Cit A A (SEQ ID NO: 180) | (0002-34) |
| H Q K W N Cit G R S R A A (SEQ ID NO: 181) | (0002-24) |
| H Q K F W Cit G R S R A A (SEQ ID NO: 182) | (0002-25) |
| H Q K Cit K Cit G R S R A A (SEQ ID NO: 183) | (0002-26) |
| H Q K W R Cit G R S Cit A A (SEQ ID NO: 184) | (0002-37) |
| H Q A W R Cit G R S Cit A A (SEQ ID NO: 185) | (0002-40) |
| H Q N Q W Cit G R S R A A (SEQ ID NO: 186) | (0002-44) |
| H Q N S K Cit G R S R A A (SEQ ID NO: 187) | (0002-45) |
| H Q K R R Cit G R S R A A (SEQ ID NO: 188) | (0102-76) |
| H Q K R F Cit G R S R A A (SEQ ID NO: 189) | (0102-77) |
| H Q K R Y Cit G R S R A A (SEQ ID NO: 190) | (0102-78) |
| H Q K R H Cit G R S R A A (SEQ ID NO: 191) | (0102-79) |
| H Q E R A Cit G S S R A A (SEQ ID NO: 192) | (020699-3) |
| H Q E K M Cit G V S R A A (SEQ ID NO: 193) | (020699-5) |
| H Q K R G Cit G W S R A A (SEQ ID NO: 194) | (0002-27) |
| H Q R R V Cit G W S R A A (SEQ ID NO: 195) | (0002-29) |
| H Q W N R Cit G W S R A A (SEQ ID NO: 196) | (0002-35) |
| H Q Q R M Cit G W S R A A (SEQ ID NO: 197) | (0002-41) |
| H Q S H R Cit G W S R A A (SEQ ID NO: 198) | (0002-39) |
| H Q F R F Cit G W S R A A (SEQ ID NO: 199) | (0002-63) |
| H Q K R R Cit G W S R A A (SEQ ID NO: 200) | (0102-75) |
| G V K G H Cit G Y P G L D (SEQ ID NO: 201) | (0101-3) |

From the above data a consensus sequence is derived of amino acids that appear to have a preference for a particular position. An XG peptide unit being preferably recognized by RA sera may therefore be represented by:

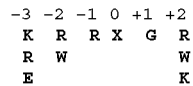

All these peptides showed good to excellent results. Especially the peptides 0002-35, 0002-36 and 0002-63 were very satisfactory. In most of the cases the cyclic variant of such a peptide reacted even better (see later). Incidentally, this is not always the case. For example, the linear peptide 0101-7 reacted with 55% of the sera. The cyclic variant of this peptide reacted with "only" 45% of 186 RA-sera. As expected, the arginine variants of these peptides (wherein the citrulline(s) is/are replaced by arginine(s)) did not react with the RA sera.

Example 5: Cyclic Variants of XG Peptides

The peptides described below were cyclisized in accordance with the cysteine-bromoacetic acid method. Several cyclic variants were tested, with in particular the cyclic variants of peptides 0002-27, 0002-29, 0002-31, 0002-36, and 0002-63 proving to be of interest.

Ring size: a number of adequately reacting peptides were used to synthesise additional cyclic peptides that each had a different ring size. Of these the 8, 9, 10, 11 and 12-mers were eventually tested. All these peptides were tested in ELISA with 48 RA sera and 8 normal sera respectively. The 8- and 9-mers reacted with some of the sera (with 22% (titre 0.47) and 28% (titre 0.5), respectively, but the titres (the OD-values found) were much lower than when larger rings were used (10-mer 33% with a titre van 0.60; 11- and 12-mer 50% with an average titre of 0.74.

TABLE 2

Results from serum-analyses using cyclic peptide 0002-36.

|  | N | % positive sera |
|---|---|---|
| RA | 318 | 71 |
| Systemic Lupus Erythematodes | 24 | 0 |
| Prim Sjögren's syndrome | 34 | 3 |
| SSc Scleroderma | 10 | 0 |
| PM, Polymyositis | 11 | 0 |
| Osteoarthritis | 29 | 0 |
| Crohn's disease | 40 | 0 |
| Colitis ulcerosa | 40 | 0 |
| Infectious diseases (malaria, chlamydia, mycoplasma, etc.) | 250 | 1 |
| Psoriasis | 10 | 0 |
| Vasculitis | 30 | 0 |
| Normal human serum | 84 | 0 |

The above table represents ELISAs with sera obtained from patients suffering from RA and from patients suffering from various other autoimmune diseases. This shows the high specificity of RA sera for a peptide such as 0002-36. Practically none of the cases showed sera obtained from other autoimmune diseases and material from normal healthy persons to be positive. The arginine variant of peptide 0002-36 (R on position 0 and +2, i.e., instead of Cit in the formula) was also tested and shown to be negative with all tested RA and normal sera.

TABLE 3

ELISA with 132 RA sera with peptide 36 compared with peptide cfc1 from [PCT/NL97/00624]:

| peptide | cfc1 (linear) | cfc1 (cyclic) | 0002-36 (linear) | 0002-36 (cyclic) |
|---|---|---|---|---|
| positive sera | 48/132 36% | 83/132 63% | 80/132 61% | 94/132 71% |

By using cyclic cfc1 as well as cyclic 0002-36 an additional 2% sensitivity may be gained (total 73%, see Table 4), which for this type of application is a welcome improvement as long as it is not accompanied by a declining specificity. The latter does not seem to be the case. Thus within the XG group of peptides there is diversity with regard to their ability to react with RA antibodies.

TABLE 4

ELISA with 186 RA sera and cyclic variants of cf1, 0002-36, and 0002-63

| peptide | cfc1 (cyclic) | 0002-63 (cyclic) | 0002-36 (cyclic) | cfc1 + 0002-36 (cyclic) |
|---|---|---|---|---|
| positive sera | 51% | 71% | 71% | 73% |

Comparing the linear and the cyclic variants of 0002-36 in two cohorts of RA sera (in total 318 sera), the cyclic variant was shown to react more frequently (and better) than the linear variant. Better, because the OD-values found with the cyclic variant were also much higher than with the linear composition. Whether the cyclic variant was created via —S—S-bonds between two cysteines, or via a thioether formed, for example, by reacting a cysteine and a bromoacetyl group (formed by reacting a thiol in the side chain of a cysteine with an N-terminal bromoacetyl group, forming a thioether), is immaterial. The N-terminal bromoacetyl group is formed, after the synthesis of the peptide, by allowing the bead-bound peptide (peptidyl-resin) to react with the N-hydroxy succinimide ester of bromoacetic acid) in the same peptide. The ring closure occurs in a phosphate-buffered aqueous acetonitril solution, pH=8.

Example 6: The Family of XnonG Peptides

Surprisingly, there were also peptides found that were not derived from (pro)filaggrin, fibrin, fibrinogen, vimentin, cytokeratin 1 and cytokeratin 9, and that were recognized by RA sera that did not or only slightly react with peptides of the XG family described above. A characteristic of these peptides is that the amino acid and the C-terminal side of the Cit is basic (R, K, H), aromatic (W, Y, F) aliphatic (M, I, V) or Cit, S or P (see Table 5), but not G. Hence the name XnonG family. Remarkably, XnonG peptides comprise relatively many positively charged amino acids on the −2, −1, +1 and +2 positions. Thus the antibodies in these RA sera react with a citrulline in a different peptide context.

The XnonG peptides mentioned all reacted with one or more XG-negative sera. For example, peptides 0107-32, 0107-35, and 0107-45 react with approximately 15-18% of the XG negative sera. An ELISA test based on one or more of these peptides induces a sensitivity increase of at least 5% (up from 73% to 78%) compared with the combination of cyclic cfc1 and cyclic 0002-36. Very importantly, none of the XnonG peptides mentioned reacted with control sera.

TABLE 5

| Peptides of the XnonG family: | |
|---|---|
| R H G R Q Cit Cit K Y I I Y (SEQ ID NO: 115) | (0107-33) |
| R H G R Q Cit Cit Cit Y I I Y (SEQ ID NO: 116) | (0107-34) |
| I R Cit Y K Cit I T N R K F (SEQ ID NO: 117) | (0107-37) |
| A R F Q M Cit H Cit R L I R (SEQ ID NO: 118) | (0107-35) |
| Q Cit Y K W Cit K I E R K R (SEQ ID NO: 119) | (0107-43) |
| K P Y T V Cit K F M R K P (SEQ ID NO: 120) | (0107-31) |
| K P Y T V Cit K F M R R P (SEQ ID NO: 121) | (0107-32) |
| R N L R L Cit R E R N H A (SEQ ID NO: 122) | (0107-36) |
| R R R Cit Y Cit R A V I T A (SEQ ID NO: 123) | (0107-38) |
| R F K S N Cit R T P N R W (SEQ ID NO: 124) | (0107-42) |
| R G K S N Cit R T Y N R W (SEQ ID NO: 125) | (0107-39) |
| R F K S N Cit R T Y N R W (SEQ ID NO: 126) | (0107-40) |
| R G K S N Cit R T P N R W (SEQ ID NO: 127) | (0107-41) |
| R W V S Q Cit R R T P T R (SEQ ID NO: 128) | (0102-71) |
| M K P R Y Cit R R I V V V (SEQ ID NO: 129) | (0102-73) |
| K S F V W Cit S H A R P R (SEQ ID NO: 130) | (0107-44) |
| Y S F V W Cit S H A R P R (SEQ ID NO: 131) | (0107-45) |
| R N M N R Cit W R G M Cit R (SEQ ID NO: 132) | (0107-30) |
| R M G R P Cit W I R F P V (SEQ ID NO: 133) | (0102-72) |
| as well as | |
| I N Cit R A S Cit K Cit H R R (SEQ ID NO: 134) | 0215-46 |
| I Cit K R L Y Cit M Cit I R R (SEQ ID NO: 135) | 0219-44 |
| K Cit Cit Y N I Cit Cit F R R N (SEQ ID NO: 136) | 0222-56 |
| R L Y F I Cit Cit R A Q T T (SEQ ID NO: 137) | 0222-57 |
| I R Q G A R Cit R G Y P K (SEQ ID NO: 138) | 0223-12 |
| Cit E R Cit V Q Cit R R P P Q (SEQ ID NO: 139) | 150202RA02 |
| Cit H Q R I T Cit V G Cit R K (SEQ ID NO: 140) | 150202RA03 |
| R I Cit R V Cit Cit T P I P R (SEQ ID NO: 141) | 061102RA01 |
| G R N Q R Y Cit L Y T I H (SEQ ID NO: 142) | 061102RA02 |
| R Cit R Q H P Cit H R I K A (SEQ ID NO: 143) | 061102RA03 |
| Cit Cit R Cit V A Cit F Cit R V R (SEQ ID NO: 144) | 061102RA05 |
| R P K Q H V Cit H T R R P (SEQ ID NO: 145) | 061102RA06 |
| R K Cit G Cit R Cit Cit T I R P (SEQ ID NO: 146) | 061102RA07 |
| R Cit Cit R N T Cit H I K Cit R (SEQ ID NO: 147) | 061102RA08 |
| R Cit Q Cit F T Cit Cit R N V V (SEQ ID NO: 148) | 061102RA09 |
| Q L V Y L Q Cit Cit Cit R R Y (SEQ ID NO: 149) | 061102RA11 |
| Q Y N R F K Cit Cit Cit R P R (SEQ ID NO: 150) | 061102RA12 |
| Cit L R H I R Cit Q T R Cit Cit (SEQ ID NO: 151) | 061102RA14 |
| P R Cit Cit Cit K Cit R Cit Cit G R (SEQ ID NO: 152) | 061102RA15 |
| R Cit Q V R Y Cit Cit L Cit R Cit (SEQ ID NO: 153) | 061102RA16 |

TABLE 5-continued

Peptides of the XnonG family:

| | |
|---|---|
| G R Cit H A H Cit P R V R Cit (SEQ ID NO: 154) | 061102RA17 |
| A R H V I R Cit Cit V P R T (SEQ ID NO: 155) | 181102RA01 |
| R Cit G H M F Cit V Y Cit F R (SEQ ID NO: 156) | 181102RA02 |
| G R N I R V Cit Cit A R Cit Cit (SEQ ID NO: 157) | 181102RA04 |
| Q I F Y L Cit Cit H R Q Cit R (SEQ ID NO: 158) | 221102RA01 |
| R Q G P I A Cit L H I R R (SEQ ID NO: 159) | 221102RA02 |
| G V Y L V R Cit L Cit M M R (SEQ ID NO: 160) | 0218-36 |
| N Cit Cit R R V Cit M Cit R I Cit (SEQ ID NO: 161) | 271102RA01 |
| K Cit R L Cit Y Cit P V R K S (SEQ ID NO: 162) | 271102RA02 |
| G R R Cit Cit L Cit R P Cit Cit R (SEQ ID NO: 163) | 271102RA03 |
| R M P H Cit H Cit S Cit R R K (SEQ ID NO: 164) | 271102RA04 |

From the above data it is possible to derive a consensus sequence of amino acids that appear to have a preference for certain positions. Therefore, a XnonG peptide unit preferably recognized by RA sera may be represented by:

```
-5 -4  3 -2 -1  0 +1 +2 +3 +4 +5
 R  R  R  R  R  X  R  R  R  R  R
    N  Y  V  Q     H  T  I  I  K
       F  I  Y              Y  P  P
       H  S  V                 N
          G
```

Experiments have shown that, for example, peptide 0107-35 in the cyclic form reacts with 18% of the sera that are not reactive with cyclic 0002-36. This sensitivity may be further increased by other peptides. For example, a further 8% may be added by cyclic peptide 0107-32. This allows the sensitivity to be increased to 80%. A similar value was found for the peptide 0107-45. In total 17 of the 52 (32%) XG-negative sera were shown to react with one or more XnonG peptides. This means that with combinations of more than 2 XG and XnonG peptides, a preferred embodiment of the invention, a sensitivity of above 80% can be achieved. This is therefore better than what can be achieved by a combination of the peptides with the formula IV, and those known from PCT/NL97/00624.

The sensitivity can be increased even further by using more peptides still. When testing the RA sera with a cyclic XG peptide (for example 0002-63 or 0002-36) together with a linear or cyclic XnonG peptide (for example 0107-35), for 318 RA sera a sensitivity of 78% was obtained. The addition of a 3rd, 4th and possibly 5th peptide increased the sensitivity to 85% (peptides 0107-32, 0107-42 respectively 0107-34). A mere 48 of the 318 RA sera did not react with one of the peptides mentioned.

Example 7: Sensitivity and Specificity of Diagnostic Tests Comprising XG and XnonG Peptide Units Using the above-described methods, seven XG peptide units were tested for reactivity with the 318 sera mentioned in Table 2 from patients suffering from rheumatoid arthritis. The specificity was determined with the aid of sera mentioned in Table 2 from control patients and normal donors. Table 6 shows the specificity and sensitivity of the individual peptide units.

TABLE 6

| XG Peptide units | Sensitivity [%] | | Specificity [%] | |
|---|---|---|---|---|
| | Linear | cyclic | linear | cyclic |
| 0002-27 | 56 | 71 | 98 | 98 |
| 0002-29 | 57 | 70 | 98 | 98 |
| 0002-31 | 51 | 69 | 98 | 98 |
| 0002-32 | 61 | 71 | 98 | 98 |
| 0002-36 | 61 | 71 | 99 | 99 |
| 0002-37 | 60 | 70 | 98 | 98 |
| 0002-63 | 60 | 71 | 98 | 98 |
| cfc1 | 36 | 56 | — | — |

In accordance with the methods described in this document, five XnonG peptide units were tested for reactivity with the same 318 sera mentioned in Table 2 from patients suffering from rheumatoid arthritis. Specificity was again determined with the aid of the sera mentioned in Table 2 from control patients and normal donors. Table 7 shows the specificity and sensitivity of the individual peptide units.

TABLE 7

| Peptide unit | Sensitivity [%] | | Specificity [%] | |
|---|---|---|---|---|
| | Linear | cyclic | linear | cyclic |
| 0107-32 | 48 | 63 | 98 | 98 |
| 0107-35 | 52 | 61 | 98 | 99 |
| 0107-45 | 51 | 69 | 98 | 99 |
| 0113-30 | 49 | 71 | 99 | 100 |
| 0218-36 | 50 | 70 | 98 | 98 |

The reactivity of the XnonG peptide units mentioned in Table 7 was tested with 80 sera from the panel of 318 sera described above that did not react with any of the XG peptide from Table 6. The percentages mentioned in table 8 therefore show the percentage of the sera that did comprise antibodies to XnonG peptide units but comprised no XG

TABLE 8

| Peptide unit | Sensitivity [%] | |
|---|---|---|
| | Linear | cyclic |
| 0107-32 | 15 | 18 |
| 0107-35 | 17 | 18 |
| 0107-45 | 16 | 18 |
| 0113-30 | 18 | 19 |
| 0218-36 | 17 | 17 |

The above results show that an increased sensitivity may be expected if each of the XG peptide units from Table 6 is combined with each of the peptide units from Table 7. All the combinations of peptide units given below were tested with a representative portion of the above-mentioned panel of 318 sera from patients suffering from rheumatoid arthritis. This experiment does in fact show that an average gain in sensitivity of 6% was obtained, bringing the total sensitivity of such a combination test to 75 to 78%.

The tested combinations of peptide units related to: peptide unit 0002-27 with 0107-32; 0002-27 with 0107-35; 0002-27 with 0107-45; 0002-27 with 0113-30; 0002-27 with 0218-36; 0002-29 with 0107-32; 0002-29 with 0107-35; 0002-29 with 0107-45; 0002-29 with 0113-30; 0002-29 with 0218-36; 0002-31 with 0107-32; 0002-31 with 0107-35; 0002-31 with 0107-45; 0002-31 with 0113-30; 0002-31 with 0218-36; 0002-32 with 0107-32; 0002-32 with 0107-35; 0002-32 with 0107-45; 0002-32 with 0113-30; 0002-32 with 0218-36; 0002-36 with 0107-32; 0002-36 with 0107-35; 0002-36 with 0107-45; 0002-36 with 0113-30; 0002-36 with 0218-36; 0002-37 with 0107-32; 0002-37 with 0107-35; 0002-37 with 0107-45; 0002-37 with 0113-30; 0002-37 with 0218-36; 0002-63 with 0107-32; 0002-63 with 0107-35; 0002-63 with 0107-45; 0002-63 with 0113-30 and finally 0002-63 with 0218-36.

With respect to the results of Table 6 and Table 8 it should also be noted that the various peptide units also detected different cohorts of sera. From this it may be deduced that the above-mentioned combinations of XG and XnonG peptide units also are capable of producing a further gain in sensitivity if a third peptide unit or even a fourth or further peptide units are added. Depending on the selected combination of peptide units, the diagnostic test according to the invention did indeed make it possible to achieve a sensitivity of 88-92%.

The invention claimed is:

1. An isolated peptide comprising a sequence with the formula (II):

(A1-A2-A3-A4-A5)-Cit-(A6)-(A7-A8-A9-A10-A11)    (II)

wherein

A1-A2-A3-A4-A5 is an amino acid sequence selected from the group consisting of:

| | |
|---|---|
| RHGRQ | (SEQ ID NO: 13) |
| IRCitYK | (SEQ ID NO: 14) |
| HGRQCit | (SEQ ID NO: 15) |
| GRQCitCit | (SEQ ID NO: 16) |
| FQMCitH | (SEQ ID NO: 17) |
| CitWRGM | (SEQ ID NO: 18) |
| ARFQM | (SEQ ID NO: 19) |
| QCitYKW | (SEQ ID NO: 20) |
| KPYTV | (SEQ ID NO: 21) |
| NRLRL | (SEQ ID NO: 22) |
| RRRCitY | (SEQ ID NO: 23) |
| RFKSN | (SEQ ID NO: 24) |
| RGKSN | (SEQ ID NO: 25) |
| RWVSQ | (SEQ ID NO: 26) |
| MKPRY | (SEQ ID NO: 27) |
| YSFVW | (SEQ ID NO: 29) |
| FQMRH | (SEQ ID NO: 30) |
| RNMNR | (SEQ ID NO: 31) |
| and | |
| RMGRP | (SEQ ID NO: 32); |

A6 represents an amino acid other than glycine;

A7-A8-A9-A10-A11 represents an amino acid sequence selected from the group consisting of:

| | |
|---|---|
| KYIIY | (SEQ ID NO: 33) |
| TNRKF | (SEQ ID NO: 34) |
| KWCitKI | (SEQ ID NO: 35) |
| CitRAVI | (SEQ ID NO: 36) |
| RCitGHS | (SEQ ID NO: 37) |
| CitGRSR | (SEQ ID NO: 38) |
| CitYIIY | (SEQ ID NO: 39) |
| CitRLIR | (SEQ ID NO: 40) |
| IERKR | (SEQ ID NO: 41) |
| FMRKP | (SEQ ID NO: 42) |
| FMRRP | (SEQ ID NO: 43) |
| ERNHA | (SEQ ID NO: 44) |
| AVITA | (SEQ ID NO: 45) |
| TPNRW | (SEQ ID NO: 46) |
| TYNRW | (SEQ ID NO: 47) |
| RTPTR | (SEQ ID NO: 48) |
| RIVVV | (SEQ ID NO: 49) |

| | | |
|---|---|---|
| RGMCitR and | (SEQ ID NO: 51) | |
| IRFPV | (SEQ ID NO: 52); | | wherein Cit refers to citrulline.

2. The peptide of claim 1, wherein A6 is selected from the group consisting of Cit, H, I, K, R, S, W, Y, M, F, V and P.

3. The peptide of claim 1, wherein the peptide is a cyclic peptide comprising a ring of at least 8 amino acids.

4. The peptide of claim 3, wherein the ring comprises at least 11 amino acids.

5. The peptide of claim 1 which comprises the peptide sequence

| | |
|---|---|
| R H G R Q Cit Cit K Y I I Y | (SEQ ID NO: 115) |
| I R Cit Y K Cit I T N R K F | (SEQ ID NO: 116) |
| R H G R Q Cit Cit Cit Y I I Y | (SEQ ID NO: 117) |
| A R F Q M Cit H Cit R L I R | (SEQ ID NO: 118) |
| Q Cit Y K W Cit K I E R K R | (SEQ ID NO: 119) |
| K P Y T V Cit K F M R K P | (SEQ ID NO: 120) |
| K P Y T V Cit K F M R R P | (SEQ ID NO: 121) |
| R N L R L Cit R E R N H A | (SEQ ID NO: 122) |
| R R R Cit Y Cit R A V I T A | (SEQ ID NO: 123) |
| R F K S N Cit R T P N R W | (SEQ ID NO: 124) |
| R G K S N Cit R T Y N R W | (SEQ ID NO: 125) |
| R F K S N Cit R T Y N R W | (SEQ ID NO: 126) |
| R G K S N Cit R T P N R W | (SEQ ID NO: 127) |
| R W V S Q Cit R R T P T R | (SEQ ID NO: 128) |
| M K P R Y Cit R R I V V V | (SEQ ID NO: 129) |
| K S F V W Cit S H A R P R | (SEQ ID NO: 130) |
| Y S F V W Cit S H A R P R | (SEQ ID NO: 131) |
| R N M N R Cit W R G M Cit R, or | (SEQ ID NO: 132) |
| R M G R P Cit W I R F P V | (SEQ ID NO: 133). |

6. A diagnostic test kit for determining the presence or absence of autoantibodies to rheumatoid arthritis, comprising a peptide of claim 1, or a mixture thereof, together with at least one further reagent.

* * * * *

SEQUENCE LISTING

```
<160> NUMBER OF SEQ ID NOS: 212

<210> SEQ ID NO 1
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 1

His Gln Lys Arg Gly Xaa Gly Trp Ser Arg Ala Ala
1               5                   10

<210> SEQ ID NO 2
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 2

His Gln Arg Arg Val Xaa Gly Trp Ser Arg Ala Ala
1               5                   10

<210> SEQ ID NO 3
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
```

<223> OTHER INFORMATION: Xaa=Citrulline

<400> SEQUENCE: 3

His Gln Arg Arg Thr Xaa Gly Gly Ser Arg Ala Ala
1               5                   10

<210> SEQ ID NO 4
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 4

His Gln Arg Lys Trp Xaa Gly Ala Ser Arg Ala Ala
1               5                   10

<210> SEQ ID NO 5
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,8
<223> OTHER INFORMATION: Xaa=Citrulline

<400> SEQUENCE: 5

His Gln Phe Arg Phe Xaa Gly Xaa Ser Arg Ala Ala
1               5                   10

<210> SEQ ID NO 6
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,10
<223> OTHER INFORMATION: Xaa=Citrulline

<400> SEQUENCE: 6

His Gln Lys Trp Arg Xaa Gly Arg Ser Xaa Ala Ala
1               5                   10

<210> SEQ ID NO 7
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 7

His Gln Phe Arg Phe Xaa Gly Trp Ser Arg Ala Ala
1               5                   10

```
<210> SEQ ID NO 8
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 8

Lys Pro Tyr Thr Val Xaa Lys Phe Met Arg Arg Pro
1               5                   10

<210> SEQ ID NO 9
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,8
<223> OTHER INFORMATION: Xaa=Citrulline

<400> SEQUENCE: 9

Ala Arg Phe Gln Met Xaa His Xaa Arg Leu Ile Arg
1               5                   10

<210> SEQ ID NO 10
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 10

Tyr Ser Phe Val Trp Xaa Ser His Ala Arg Pro Arg
1               5                   10

<210> SEQ ID NO 11
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 8
<223> OTHER INFORMATION: Xaa=Citrulline

<400> SEQUENCE: 11

Ala Arg Phe Gln Met Arg His Xaa Arg Leu Ile Arg
1               5                   10

<210> SEQ ID NO 12
<211> LENGTH: 12
<212> TYPE: PRT
<213> ORGANISM: Artificial sequence
<220> FEATURE:
<223> OTHER INFORMATION: Derived from known cDNA sequences of human
```

```
        fillagrin
<220> FEATURE:
<221> NAME/KEY: VARIANT
<222> LOCATION: 6
<223> OTHER INFORMATION: Xaa=Citrulline

<400> SEQUENCE: 12

Arg Asn Leu Arg Leu Xaa Arg Glu Arg Asn His Ala
1               5                   10

<210> SEQ ID NO 13
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 13

Arg His Gly Arg Gln
1               5

<210> SEQ ID NO 14
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3
<223> OTHER INFORMATION: Xaa=Citrulline

<400> SEQUENCE: 14

Ile Arg Xaa Tyr Lys
1               5

<210> SEQ ID NO 15
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 5
<223> OTHER INFORMATION: Xaa=Citrulline

<400> SEQUENCE: 15

His Gly Arg Gln Xaa
1               5

<210> SEQ ID NO 16
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 4,5
<223> OTHER INFORMATION: Xaa=Citrulline

<400> SEQUENCE: 16

Gly Arg Gln Xaa Xaa
1               5
```

```
<210> SEQ ID NO 17
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 4
<223> OTHER INFORMATION: Xaa=Citrulline

<400> SEQUENCE: 17

Phe Gln Met Xaa His
1               5

<210> SEQ ID NO 18
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 18

Xaa Trp Arg Gly Met
1               5

<210> SEQ ID NO 19
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 19

Ala Arg Phe Gln Met
1               5

<210> SEQ ID NO 20
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2
<223> OTHER INFORMATION: Xaa=Citrulline

<400> SEQUENCE: 20

Gln Xaa Tyr Lys Trp
1               5

<210> SEQ ID NO 21
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 21
```

-continued

```
Lys Pro Tyr Thr Val
1               5

<210> SEQ ID NO 22
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 22

Arg Asn Leu Arg Leu
1               5

<210> SEQ ID NO 23
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 4
<223> OTHER INFORMATION: Xaa=Citrulline

<400> SEQUENCE: 23

Arg Arg Arg Xaa Tyr
1               5

<210> SEQ ID NO 24
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 24

Arg Phe Lys Ser Asn
1               5

<210> SEQ ID NO 25
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 25

Arg Gly Lys Ser Asn
1               5

<210> SEQ ID NO 26
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 26

Arg Trp Val Ser Gln
1               5

<210> SEQ ID NO 27
```

```
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 27

Met Lys Pro Arg Tyr
1               5

<210> SEQ ID NO 28
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 28

Lys Ser Phe Val Trp
1               5

<210> SEQ ID NO 29
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 29

Tyr Ser Phe Val Trp
1               5

<210> SEQ ID NO 30
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 30

Phe Gln Met Arg His
1               5

<210> SEQ ID NO 31
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 31

Arg Asn Met Asn Arg
1               5

<210> SEQ ID NO 32
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 32
```

```
Arg Met Gly Arg Pro
1               5

<210> SEQ ID NO 33
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 33

Lys Tyr Ile Ile Tyr
1               5

<210> SEQ ID NO 34
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 34

Thr Asn Arg Lys Phe
1               5

<210> SEQ ID NO 35
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3
<223> OTHER INFORMATION: Xaa=Citrulline

<400> SEQUENCE: 35

Lys Trp Xaa Lys Ile
1               5

<210> SEQ ID NO 36
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 36

Xaa Arg Ala Val Ile
1               5

<210> SEQ ID NO 37
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2
<223> OTHER INFORMATION: Xaa=Citrulline
```

-continued

<400> SEQUENCE: 37

Arg Xaa Gly His Ser
1               5

<210> SEQ ID NO 38
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 38

Xaa Gly Arg Ser Arg
1               5

<210> SEQ ID NO 39
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 39

Xaa Tyr Ile Ile Tyr
1               5

<210> SEQ ID NO 40
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 40

Xaa Arg Leu Ile Arg
1               5

<210> SEQ ID NO 41
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 41

Ile Glu Arg Lys Arg
1               5

<210> SEQ ID NO 42
<211> LENGTH: 5
<212> TYPE: PRT
<213> ORGANISM: Artificial sequence

```
<220> FEATURE:
<223> OTHER INFORMATION: Derived from known cDNA sequences of human
      fillagrin

<400> SEQUENCE: 42

Phe Met Arg Lys Pro
1               5

<210> SEQ ID NO 43
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 43

Phe Met Arg Arg Pro
1               5

<210> SEQ ID NO 44
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 44

Glu Arg Asn His Ala
1               5

<210> SEQ ID NO 45
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 45

Ala Val Ile Thr Ala
1               5

<210> SEQ ID NO 46
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 46

Thr Pro Asn Arg Trp
1               5

<210> SEQ ID NO 47
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 47

Thr Tyr Asn Arg Trp
1               5
```

```
<210> SEQ ID NO 48
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 48

Arg Thr Pro Thr Arg
1               5

<210> SEQ ID NO 49
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 49

Arg Ile Val Val Val
1               5

<210> SEQ ID NO 50
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 50

His Ala Arg Pro Arg
1               5

<210> SEQ ID NO 51
<211> LENGTH: 5
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 4
<223> OTHER INFORMATION: Xaa=Citrulline

<400> SEQUENCE: 51

Arg Gly Met Xaa Arg
1               5

<210> SEQ ID NO 52
<211> LENGTH: 5
<212> TYPE: PRT
<213> ORGANISM: Artificial sequence
<220> FEATURE:
<223> OTHER INFORMATION: Derived from known cDNA sequences of human
      fillagrin

<400> SEQUENCE: 52

Ile Arg Phe Pro Val
1               5

<210> SEQ ID NO 53
<211> LENGTH: 6
<212> TYPE: PRT
<213> ORGANISM: Artificial sequence
```

```
<220> FEATURE:
<223> OTHER INFORMATION: Derived from known cDNA sequences of human
      fillagrin
<220> FEATURE:
<221> NAME/KEY: VARIANT
<222> LOCATION: 3
<223> OTHER INFORMATION: Xaa=Citrulline

<400> SEQUENCE: 53

Ile Asn Xaa Arg Ala Ser
1               5

<210> SEQ ID NO 54
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2
<223> OTHER INFORMATION: Xaa=Citrulline

<400> SEQUENCE: 54

Ile Xaa Lys Arg Leu Tyr
1               5

<210> SEQ ID NO 55
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,3
<223> OTHER INFORMATION: Xaa=Citrulline

<400> SEQUENCE: 55

Lys Xaa Xaa Tyr Asn Ile
1               5

<210> SEQ ID NO 56
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 56

Arg Leu Tyr Phe Ile Xaa
1               5

<210> SEQ ID NO 57
<211> LENGTH: 6
<212> TYPE: PRT
<213> ORGANISM: Artificial sequence
<220> FEATURE:
<223> OTHER INFORMATION: Derived from known cDNA sequences of human
      fillagrin

<400> SEQUENCE: 57

Ile Arg Gln Gly Ala Arg
```

```
1               5

<210> SEQ ID NO 58
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1,4
<223> OTHER INFORMATION: Xaa=Citrulline

<400> SEQUENCE: 58

Xaa Glu Arg Xaa Val Gln
1               5

<210> SEQ ID NO 59
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 59

Xaa His Gln Arg Ile Thr
1               5

<210> SEQ ID NO 60
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,6
<223> OTHER INFORMATION: Xaa=Citrulline

<400> SEQUENCE: 60

Arg Ile Xaa Arg Val Xaa
1               5

<210> SEQ ID NO 61
<211> LENGTH: 6
<212> TYPE: PRT
<213> ORGANISM: Artificial sequence
<220> FEATURE:
<223> OTHER INFORMATION: Derived from known cDNA sequences of human
      fillagrin

<400> SEQUENCE: 61

Gly Arg Asn Gln Arg Tyr
1               5

<210> SEQ ID NO 62
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
```

```
<221> NAME/KEY: VARIANT
<222> LOCATION: 2
<223> OTHER INFORMATION: Xaa=Citrulline

<400> SEQUENCE: 62

Arg Xaa Arg Gln His Pro
1               5

<210> SEQ ID NO 63
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1,2,4
<223> OTHER INFORMATION: Xaa=Citrulline

<400> SEQUENCE: 63

Xaa Xaa Arg Xaa Val Ala
1               5

<210> SEQ ID NO 64
<211> LENGTH: 6
<212> TYPE: PRT
<213> ORGANISM: Artificial sequence
<220> FEATURE:
<223> OTHER INFORMATION: Derived from known cDNA sequences of human
      fillagrin

<400> SEQUENCE: 64

Arg Pro Lys Gln His Val
1               5

<210> SEQ ID NO 65
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,5
<223> OTHER INFORMATION: Xaa=Citrulline

<400> SEQUENCE: 65

Arg Lys Xaa Gly Xaa Arg
1               5

<210> SEQ ID NO 66
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,3
<223> OTHER INFORMATION: Xaa=Citrulline

<400> SEQUENCE: 66

Arg Xaa Xaa Arg Asn Thr
1               5

<210> SEQ ID NO 67
```

```
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,4
<223> OTHER INFORMATION: Xaa=Citrulline

<400> SEQUENCE: 67

Arg Xaa Gln Xaa Phe Thr
1               5

<210> SEQ ID NO 68
<211> LENGTH: 6
<212> TYPE: PRT
<213> ORGANISM: Artificial sequence
<220> FEATURE:
<223> OTHER INFORMATION: Derived from known cDNA sequences of human
      fillagrin

<400> SEQUENCE: 68

Gln Leu Val Tyr Leu Gln
1               5

<210> SEQ ID NO 69
<211> LENGTH: 6
<212> TYPE: PRT
<213> ORGANISM: Artificial sequence
<220> FEATURE:
<223> OTHER INFORMATION: Derived from known cDNA sequences of human
      fillagrin

<400> SEQUENCE: 69

Gln Tyr Asn Arg Phe Lys
1               5

<210> SEQ ID NO 70
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 70

Xaa Leu Arg His Ile Arg
1               5

<210> SEQ ID NO 71
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,4,5
<223> OTHER INFORMATION: Xaa=Citrulline

<400> SEQUENCE: 71

Pro Arg Xaa Xaa Xaa Lys
1               5
```

<210> SEQ ID NO 72
<211> LENGTH: 6
<212> TYPE: PRT
<213> ORGANISM: Artificial sequence
<220> FEATURE:
<223> OTHER INFORMATION: Derived from known cDNA sequences of human
     fillagrin
<220> FEATURE:
<221> NAME/KEY: VARIANT
<222> LOCATION: 2
<223> OTHER INFORMATION: Xaa=Citrulline

<400> SEQUENCE: 72

Arg Xaa Gln Val Arg Tyr
1               5

<210> SEQ ID NO 73
<211> LENGTH: 6
<212> TYPE: PRT
<213> ORGANISM: Artificial sequence
<220> FEATURE:
<223> OTHER INFORMATION: Derived from known cDNA sequences of human
     fillagrin
<220> FEATURE:
<221> NAME/KEY: VARIANT
<222> LOCATION: 3
<223> OTHER INFORMATION: Xaa=Citrulline

<400> SEQUENCE: 73

Gly Arg Xaa His Ala His
1               5

<210> SEQ ID NO 74
<211> LENGTH: 6
<212> TYPE: PRT
<213> ORGANISM: Artificial sequence
<220> FEATURE:
<223> OTHER INFORMATION: Derived from known cDNA sequences of human
     fillagrin

<400> SEQUENCE: 74

Ala Arg His Val Ile Arg
1               5

<210> SEQ ID NO 75
<211> LENGTH: 6
<212> TYPE: PRT
<213> ORGANISM: Artificial sequence
<220> FEATURE:
<223> OTHER INFORMATION: Derived from known cDNA sequences of human
     fillagrin
<220> FEATURE:
<221> NAME/KEY: VARIANT
<222> LOCATION: 2
<223> OTHER INFORMATION: Xaa=Citrulline

<400> SEQUENCE: 75

Arg Xaa Gly His Met Phe
1               5

<210> SEQ ID NO 76
<211> LENGTH: 6
<212> TYPE: PRT
<213> ORGANISM: Artificial sequence
<220> FEATURE:
<223> OTHER INFORMATION: Derived from known cDNA sequences of human
     fillagrin

<400> SEQUENCE: 76

```
Gly Arg Asn Ile Arg Val
1               5

<210> SEQ ID NO 77
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 77

Gln Ile Phe Tyr Leu Xaa
1               5

<210> SEQ ID NO 78
<211> LENGTH: 6
<212> TYPE: PRT
<213> ORGANISM: Artificial sequence
<220> FEATURE:
<223> OTHER INFORMATION: Derived from known cDNA sequences of human
      fillagrin

<400> SEQUENCE: 78

Arg Gln Gly Pro Ile Ala
1               5

<210> SEQ ID NO 79
<211> LENGTH: 6
<212> TYPE: PRT
<213> ORGANISM: Artificial sequence
<220> FEATURE:
<223> OTHER INFORMATION: Derived from known cDNA sequences of human
      fillagrin

<400> SEQUENCE: 79

Gly Val Tyr Leu Val Arg
1               5

<210> SEQ ID NO 80
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,3
<223> OTHER INFORMATION: Xaa=Citrulline

<400> SEQUENCE: 80

Asn Xaa Xaa Arg Arg Val
1               5

<210> SEQ ID NO 81
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,5
```

<223> OTHER INFORMATION: Xaa=Citrulline

<400> SEQUENCE: 81

Lys Xaa Arg Leu Xaa Tyr
1               5

<210> SEQ ID NO 82
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 4,5
<223> OTHER INFORMATION: Xaa=Citrulline

<400> SEQUENCE: 82

Gly Arg Arg Xaa Xaa Leu
1               5

<210> SEQ ID NO 83
<211> LENGTH: 6
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 5
<223> OTHER INFORMATION: Xaa=Citrulline

<400> SEQUENCE: 83

Arg Met Pro His Xaa His
1               5

<210> SEQ ID NO 84
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 84

Xaa His Arg Arg
1

<210> SEQ ID NO 85
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 85

Xaa Ile Arg Arg
1

```
<210> SEQ ID NO 86
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 86

Phe Arg Arg Asn
1

<210> SEQ ID NO 87
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 87

Ala Gln Thr Thr
1

<210> SEQ ID NO 88
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 88

Gly Tyr Pro Lys
1

<210> SEQ ID NO 89
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 89

Arg Pro Pro Gln
1

<210> SEQ ID NO 90
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2
<223> OTHER INFORMATION: Xaa=Citrulline

<400> SEQUENCE: 90

Gly Xaa Arg Lys
1

<210> SEQ ID NO 91
<211> LENGTH: 4
<212> TYPE: PRT
<213> ORGANISM: Artificial sequence
```

```
<220> FEATURE:
<223> OTHER INFORMATION: Derived from known cDNA sequences of human
      fillagrin

<400> SEQUENCE: 91

Pro Ile Pro Arg
1

<210> SEQ ID NO 92
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 92

Tyr Thr Ile His
1

<210> SEQ ID NO 93
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 93

Arg Ile Lys Ala
1

<210> SEQ ID NO 94
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 94

Xaa Arg Val Arg
1

<210> SEQ ID NO 95
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 95

Thr Arg Arg Pro
1

<210> SEQ ID NO 96
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 96
```

```
Thr Ile Arg Pro
1

<210> SEQ ID NO 97
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3
<223> OTHER INFORMATION: Xaa=Citrulline

<400> SEQUENCE: 97

Ile Lys Xaa Arg
1

<210> SEQ ID NO 98
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 98

Arg Asn Val Val
1

<210> SEQ ID NO 99
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 99

Xaa Arg Arg Tyr
1

<210> SEQ ID NO 100
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 100

Xaa Arg Pro Arg
1

<210> SEQ ID NO 101
<211> LENGTH: 4
<212> TYPE: PRT
<213> ORGANISM: Artificial sequence
<220> FEATURE:
<223> OTHER INFORMATION: Derived from known cDNA sequences of human
```

```
        fillagrin
<220> FEATURE:
<221> NAME/KEY: VARIANT
<222> LOCATION: 3,4
<223> OTHER INFORMATION: Xaa=Citrulline

<400> SEQUENCE: 101

Thr Arg Xaa Xaa
1

<210> SEQ ID NO 102
<211> LENGTH: 4
<212> TYPE: PRT
<213> ORGANISM: Artificial sequence
<220> FEATURE:
<223> OTHER INFORMATION: Derived from known cDNA sequences of human
        fillagrin
<220> FEATURE:
<221> NAME/KEY: VARIANT
<222> LOCATION: 1,2
<223> OTHER INFORMATION: Xaa=Citrulline

<400> SEQUENCE: 102

Xaa Xaa Gly Arg
1

<210> SEQ ID NO 103
<211> LENGTH: 4
<212> TYPE: PRT
<213> ORGANISM: Artificial sequence
<220> FEATURE:
<223> OTHER INFORMATION: Derived from known cDNA sequences of human
        fillagrin
<220> FEATURE:
<221> NAME/KEY: VARIANT
<222> LOCATION: 2,4
<223> OTHER INFORMATION: Xaa=Citrulline

<400> SEQUENCE: 103

Leu Xaa Arg Xaa
1

<210> SEQ ID NO 104
<211> LENGTH: 4
<212> TYPE: PRT
<213> ORGANISM: Artificial sequence
<220> FEATURE:
<223> OTHER INFORMATION: Derived from known cDNA sequences of human
        fillagrin
<220> FEATURE:
<221> NAME/KEY: VARIANT
<222> LOCATION: 4
<223> OTHER INFORMATION: Xaa=Citrulline

<400> SEQUENCE: 104

Arg Val Arg Xaa
1

<210> SEQ ID NO 105
<211> LENGTH: 4
<212> TYPE: PRT
<213> ORGANISM: Artificial sequence
<220> FEATURE:
<223> OTHER INFORMATION: Derived from known cDNA sequences of human
        fillagrin

<400> SEQUENCE: 105

Val Pro Arg Thr
1
```

```
<210> SEQ ID NO 106
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2
<223> OTHER INFORMATION: Xaa=Citrulline

<400> SEQUENCE: 106

Tyr Xaa Phe Arg
1

<210> SEQ ID NO 107
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,4
<223> OTHER INFORMATION: Xaa=Citrulline

<400> SEQUENCE: 107

Ala Arg Xaa Xaa
1

<210> SEQ ID NO 108
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3
<223> OTHER INFORMATION: Xaa=Citrulline

<400> SEQUENCE: 108

Arg Gln Xaa Arg
1

<210> SEQ ID NO 109
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 109

His Ile Arg Arg
1

<210> SEQ ID NO 110
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
```

```
<223> OTHER INFORMATION: Xaa=Citrulline

<400> SEQUENCE: 110

Xaa Met Met Arg
1

<210> SEQ ID NO 111
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1,4
<223> OTHER INFORMATION: Xaa=Citrulline

<400> SEQUENCE: 111

Xaa Arg Ile Xaa
1

<210> SEQ ID NO 112
<211> LENGTH: 4
<212> TYPE: PRT
<213> ORGANISM: Artificial sequence
<220> FEATURE:
<223> OTHER INFORMATION: Derived from known cDNA sequences of human
      fillagrin

<400> SEQUENCE: 112

Val Arg Lys Ser
1

<210> SEQ ID NO 113
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,3
<223> OTHER INFORMATION: Xaa=Citrulline

<400> SEQUENCE: 113

Pro Xaa Xaa Arg
1

<210> SEQ ID NO 114
<211> LENGTH: 4
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1
<223> OTHER INFORMATION: Xaa=Citrulline

<400> SEQUENCE: 114

Xaa Arg Arg Lys
1

<210> SEQ ID NO 115
<211> LENGTH: 12
<212> TYPE: PRT
```

```
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,7
<223> OTHER INFORMATION: Xaa=Citrulline

<400> SEQUENCE: 115

Arg His Gly Arg Gln Xaa Xaa Lys Tyr Ile Ile Tyr
1               5                   10

<210> SEQ ID NO 116
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,6
<223> OTHER INFORMATION: Xaa=Citrulline

<400> SEQUENCE: 116

Ile Arg Xaa Tyr Lys Xaa Ile Thr Asn Arg Lys Phe
1               5                   10

<210> SEQ ID NO 117
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,7,8
<223> OTHER INFORMATION: Xaa=Citrulline

<400> SEQUENCE: 117

Arg His Gly Arg Gln Xaa Xaa Xaa Tyr Ile Ile Tyr
1               5                   10

<210> SEQ ID NO 118
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,8
<223> OTHER INFORMATION: Xaa=Citrulline

<400> SEQUENCE: 118

Ala Arg Phe Gln Met Xaa His Xaa Arg Leu Ile Arg
1               5                   10

<210> SEQ ID NO 119
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,6
```

<223> OTHER INFORMATION: Xaa=Citrulline

<400> SEQUENCE: 119

Gln Xaa Tyr Lys Trp Xaa Lys Ile Glu Arg Lys Arg
1               5                   10

<210> SEQ ID NO 120
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 120

Lys Pro Tyr Thr Val Xaa Lys Phe Met Arg Lys Pro
1               5                   10

<210> SEQ ID NO 121
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 121

Lys Pro Tyr Thr Val Xaa Lys Phe Met Arg Arg Pro
1               5                   10

<210> SEQ ID NO 122
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 122

Arg Asn Leu Arg Leu Xaa Arg Glu Arg Asn His Ala
1               5                   10

<210> SEQ ID NO 123
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 4,6
<223> OTHER INFORMATION: Xaa=Citrulline

<400> SEQUENCE: 123

Arg Arg Arg Xaa Tyr Xaa Arg Ala Val Ile Thr Ala
1               5                   10

```
<210> SEQ ID NO 124
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 124

Arg Phe Lys Ser Asn Xaa Arg Thr Pro Asn Arg Trp
1               5                   10

<210> SEQ ID NO 125
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 125

Arg Gly Lys Ser Asn Xaa Arg Thr Tyr Asn Arg Trp
1               5                   10

<210> SEQ ID NO 126
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 126

Arg Phe Lys Ser Asn Xaa Arg Thr Tyr Asn Arg Trp
1               5                   10

<210> SEQ ID NO 127
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 127

Arg Gly Lys Ser Asn Xaa Arg Thr Pro Asn Arg Trp
1               5                   10

<210> SEQ ID NO 128
<211> LENGTH: 12
<212> TYPE: PRT
<213> ORGANISM: Artificial sequence
<220> FEATURE:
<223> OTHER INFORMATION: Derived from known cDNA sequences of human
```

```
            fillagrin
<220> FEATURE:
<221> NAME/KEY: VARIANT
<222> LOCATION: 6
<223> OTHER INFORMATION: Xaa=Citrulline

<400> SEQUENCE: 128

Arg Trp Val Ser Gln Xaa Arg Arg Thr Pro Thr Arg
1               5                   10

<210> SEQ ID NO 129
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 129

Met Lys Pro Arg Tyr Xaa Arg Arg Ile Val Val Val
1               5                   10

<210> SEQ ID NO 130
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 130

Lys Ser Phe Val Trp Xaa Ser His Ala Arg Pro Arg
1               5                   10

<210> SEQ ID NO 131
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 131

Tyr Ser Phe Val Trp Xaa Ser His Ala Arg Pro Arg
1               5                   10

<210> SEQ ID NO 132
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,11
<223> OTHER INFORMATION: Xaa=Citrulline

<400> SEQUENCE: 132
```

Arg Asn Met Asn Arg Xaa Trp Arg Gly Met Xaa Arg
1               5                   10

<210> SEQ ID NO 133
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 133

Arg Met Gly Arg Pro Xaa Trp Ile Arg Phe Pro Val
1               5                   10

<210> SEQ ID NO 134
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,7,9
<223> OTHER INFORMATION: Xaa=Citrulline

<400> SEQUENCE: 134

Ile Asn Xaa Arg Ala Ser Xaa Lys Xaa His Arg Arg
1               5                   10

<210> SEQ ID NO 135
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,7,9
<223> OTHER INFORMATION: Xaa=Citrulline

<400> SEQUENCE: 135

Ile Xaa Lys Arg Leu Tyr Xaa Met Xaa Ile Arg Arg
1               5                   10

<210> SEQ ID NO 136
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,3,7,8
<223> OTHER INFORMATION: Xaa=Citrulline

<400> SEQUENCE: 136

Lys Xaa Xaa Tyr Asn Ile Xaa Xaa Phe Arg Arg Asn
1               5                   10

<210> SEQ ID NO 137
<211> LENGTH: 12

<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,7
<223> OTHER INFORMATION: Xaa=Citrulline

<400> SEQUENCE: 137

Arg Leu Tyr Phe Ile Xaa Xaa Arg Ala Gln Thr Thr
1               5                   10

<210> SEQ ID NO 138
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 7
<223> OTHER INFORMATION: Xaa=Citrulline

<400> SEQUENCE: 138

Ile Arg Gln Gly Ala Arg Xaa Arg Gly Tyr Pro Lys
1               5                   10

<210> SEQ ID NO 139
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1,4,7
<223> OTHER INFORMATION: Xaa=Citrulline

<400> SEQUENCE: 139

Xaa Glu Arg Xaa Val Gln Xaa Arg Arg Pro Pro Gln
1               5                   10

<210> SEQ ID NO 140
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1,7,10
<223> OTHER INFORMATION: Xaa=Citrulline

<400> SEQUENCE: 140

Xaa His Gln Arg Ile Thr Xaa Val Gly Xaa Arg Lys
1               5                   10

<210> SEQ ID NO 141
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT

```
<222> LOCATION: 3,6,7
<223> OTHER INFORMATION: Xaa=Citrulline

<400> SEQUENCE: 141

Arg Ile Xaa Arg Val Xaa Xaa Thr Pro Ile Pro Arg
1               5                   10

<210> SEQ ID NO 142
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 7
<223> OTHER INFORMATION: Xaa=Citrulline

<400> SEQUENCE: 142

Gly Arg Asn Gln Arg Tyr Xaa Leu Tyr Thr Ile His
1               5                   10

<210> SEQ ID NO 143
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,7
<223> OTHER INFORMATION: Xaa=Citrulline

<400> SEQUENCE: 143

Arg Xaa Arg Gln His Pro Xaa His Arg Ile Lys Ala
1               5                   10

<210> SEQ ID NO 144
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1,2,4,7,9
<223> OTHER INFORMATION: Xaa=Citrulline

<400> SEQUENCE: 144

Xaa Xaa Arg Xaa Val Ala Xaa Phe Xaa Arg Val Arg
1               5                   10

<210> SEQ ID NO 145
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 7
<223> OTHER INFORMATION: Xaa=Citrulline

<400> SEQUENCE: 145

Arg Pro Lys Gln His Val Xaa His Thr Arg Arg Pro
1               5                   10
```

<210> SEQ ID NO 146
<211> LENGTH: 12
<212> TYPE: PRT
<213> ORGANISM: Artificial sequence
<220> FEATURE:
<223> OTHER INFORMATION: Derived from known cDNA sequences of human
    fillagrin
<220> FEATURE:
<221> NAME/KEY: VARIANT
<222> LOCATION: 3,5,7,8
<223> OTHER INFORMATION: Xaa=Citrulline

<400> SEQUENCE: 146

Arg Lys Xaa Gly Xaa Arg Xaa Xaa Thr Ile Arg Pro
1               5                   10

<210> SEQ ID NO 147
<211> LENGTH: 12
<212> TYPE: PRT
<213> ORGANISM: Artificial sequence
<220> FEATURE:
<223> OTHER INFORMATION: Derived from known cDNA sequences of human
    fillagrin
<220> FEATURE:
<221> NAME/KEY: VARIANT
<222> LOCATION: 2,3,7,11
<223> OTHER INFORMATION: Xaa=Citrulline

<400> SEQUENCE: 147

Arg Xaa Xaa Arg Asn Thr Xaa His Ile Lys Xaa Arg
1               5                   10

<210> SEQ ID NO 148
<211> LENGTH: 12
<212> TYPE: PRT
<213> ORGANISM: Artificial sequence
<220> FEATURE:
<223> OTHER INFORMATION: Derived from known cDNA sequences of human
    fillagrin
<220> FEATURE:
<221> NAME/KEY: VARIANT
<222> LOCATION: 2,4,7,8
<223> OTHER INFORMATION: Xaa=Citrulline

<400> SEQUENCE: 148

Arg Xaa Gln Xaa Phe Thr Xaa Xaa Arg Asn Val Val
1               5                   10

<210> SEQ ID NO 149
<211> LENGTH: 12
<212> TYPE: PRT
<213> ORGANISM: Artificial sequence
<220> FEATURE:
<223> OTHER INFORMATION: Derived from known cDNA sequences of human
    fillagrin
<220> FEATURE:
<221> NAME/KEY: VARIANT
<222> LOCATION: 7,8,9
<223> OTHER INFORMATION: Xaa=Citrulline

<400> SEQUENCE: 149

Gln Leu Val Tyr Leu Gln Xaa Xaa Xaa Arg Arg Tyr
1               5                   10

<210> SEQ ID NO 150
<211> LENGTH: 12
<212> TYPE: PRT
<213> ORGANISM: Artificial sequence
<220> FEATURE:

```
<223> OTHER INFORMATION: Derived from known cDNA sequences of human
      fillagrin
<220> FEATURE:
<221> NAME/KEY: VARIANT
<222> LOCATION: 7,8,9
<223> OTHER INFORMATION: Xaa=Citrulline

<400> SEQUENCE: 150

Gln Tyr Asn Arg Phe Lys Xaa Xaa Xaa Arg Pro Arg
1               5                  10

<210> SEQ ID NO 151
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1,7,11,12
<223> OTHER INFORMATION: Xaa=Citrulline

<400> SEQUENCE: 151

Xaa Leu Arg His Ile Arg Xaa Gln Thr Arg Xaa Xaa
1               5                  10

<210> SEQ ID NO 152
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,4,5,7,9,10
<223> OTHER INFORMATION: Xaa=Citrulline

<400> SEQUENCE: 152

Pro Arg Xaa Xaa Xaa Lys Xaa Arg Xaa Xaa Gly Arg
1               5                  10

<210> SEQ ID NO 153
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,7,8,10,12
<223> OTHER INFORMATION: Xaa=Citrulline

<400> SEQUENCE: 153

Arg Xaa Gln Val Arg Tyr Xaa Xaa Leu Xaa Arg Xaa
1               5                  10

<210> SEQ ID NO 154
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,7,12
<223> OTHER INFORMATION: Xaa=Citrulline
```

```
<400> SEQUENCE: 154

Gly Arg Xaa His Ala His Xaa Pro Arg Val Arg Xaa
1               5                   10

<210> SEQ ID NO 155
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 7,8
<223> OTHER INFORMATION: Xaa=Citrulline

<400> SEQUENCE: 155

Ala Arg His Val Ile Arg Xaa Xaa Val Pro Arg Thr
1               5                   10

<210> SEQ ID NO 156
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,7,10
<223> OTHER INFORMATION: Xaa=Citrulline

<400> SEQUENCE: 156

Arg Xaa Gly His Met Phe Xaa Val Tyr Xaa Phe Arg
1               5                   10

<210> SEQ ID NO 157
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 7,8,11,12
<223> OTHER INFORMATION: Xaa=Citrulline

<400> SEQUENCE: 157

Gly Arg Asn Ile Arg Val Xaa Xaa Ala Arg Xaa Xaa
1               5                   10

<210> SEQ ID NO 158
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,7,11
<223> OTHER INFORMATION: Xaa=Citrulline

<400> SEQUENCE: 158

Gln Ile Phe Tyr Leu Xaa Xaa His Arg Gln Xaa Arg
1               5                   10

<210> SEQ ID NO 159
```

```
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 7
<223> OTHER INFORMATION: Xaa=Citrulline

<400> SEQUENCE: 159

Arg Gln Gly Pro Ile Ala Xaa Leu His Ile Arg Arg
1               5                   10

<210> SEQ ID NO 160
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 7,9
<223> OTHER INFORMATION: Xaa=Citrulline

<400> SEQUENCE: 160

Gly Val Tyr Leu Val Arg Xaa Leu Xaa Met Met Arg
1               5                   10

<210> SEQ ID NO 161
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,3,7,9,12
<223> OTHER INFORMATION: Xaa=Citrulline

<400> SEQUENCE: 161

Asn Xaa Xaa Arg Arg Val Xaa Met Xaa Arg Ile Xaa
1               5                   10

<210> SEQ ID NO 162
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 2,5,7
<223> OTHER INFORMATION: Xaa=Citrulline

<400> SEQUENCE: 162

Lys Xaa Arg Leu Xaa Tyr Xaa Pro Val Arg Lys Ser
1               5                   10

<210> SEQ ID NO 163
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
```

<221> NAME/KEY: VARIANT
<222> LOCATION: 4,5,7,10,11
<223> OTHER INFORMATION: Xaa=Citrulline

<400> SEQUENCE: 163

Gly Arg Arg Xaa Xaa Leu Xaa Arg Pro Xaa Xaa Arg
1               5                   10

<210> SEQ ID NO 164
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 5,7,9
<223> OTHER INFORMATION: Xaa=Citrulline

<400> SEQUENCE: 164

Arg Met Pro His Xaa His Xaa Ser Xaa Arg Arg Lys
1               5                   10

<210> SEQ ID NO 165
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 165

His Gln Arg Lys Trp Xaa Gly Ala Ser Arg Ala Ala
1               5                   10

<210> SEQ ID NO 166
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 166

His Gln His Trp Arg Xaa Gly Ala Ser Arg Ala Ala
1               5                   10

<210> SEQ ID NO 167
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,8
<223> OTHER INFORMATION: Xaa=Citrulline

<400> SEQUENCE: 167

His Gln Phe Arg Phe Xaa Gly Xaa Ser Arg Ala Ala

<210> SEQ ID NO 168
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 168

His Gln Glu Arg Arg Xaa Gly Glu Ser Arg Ala Ala
1               5                   10

<210> SEQ ID NO 169
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 169

His Gln Lys Trp Arg Xaa Gly Phe Ser Arg Ala Ala
1               5                   10

<210> SEQ ID NO 170
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 170

His Gln Arg Trp Lys Xaa Gly Gly Ser Arg Ala Ala
1               5                   10

<210> SEQ ID NO 171
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 171

His Gln Arg Arg Thr Xaa Gly Gly Ser Arg Ala Ala
1               5                   10

<210> SEQ ID NO 172
<211> LENGTH: 12
<212> TYPE: PRT
<213> ORGANISM: Artificial sequence

```
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 172

His Gln Arg Arg Gly Xaa Gly Gly Ser Arg Ala Ala
1               5                   10

<210> SEQ ID NO 173
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,6
<223> OTHER INFORMATION: Xaa=Citrulline

<400> SEQUENCE: 173

His Gln Xaa Phe Arg Xaa Gly His Ser Arg Ala Ala
1               5                   10

<210> SEQ ID NO 174
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 174

Gly Phe Phe Ser Ala Xaa Gly His Arg Pro Leu Asp
1               5                   10

<210> SEQ ID NO 175
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 175

His Gln Glu Arg Gly Xaa Gly Lys Ser Arg Ala Ala
1               5                   10

<210> SEQ ID NO 176
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline
```

<400> SEQUENCE: 176

His Gln Glu Lys Arg Xaa Gly Lys Ser Arg Ala Ala
1               5                   10

<210> SEQ ID NO 177
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 177

His Gln Arg Trp Leu Xaa Gly Lys Ser Arg Ala Ala
1               5                   10

<210> SEQ ID NO 178
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 178

His Gln Lys Arg Asn Xaa Gly Lys Ser Arg Ala Ala
1               5                   10

<210> SEQ ID NO 179
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 179

Glu Gly Gly Gly Val Xaa Gly Pro Arg Val Val Glu
1               5                   10

<210> SEQ ID NO 180
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 180

His Gln Trp Arg His Xaa Gly Arg Ser Arg Ala Ala
1               5                   10

```
<210> SEQ ID NO 181
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 181

His Gln Lys Trp Asn Xaa Gly Arg Ser Arg Ala Ala
1               5                   10

<210> SEQ ID NO 182
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 182

His Gln Lys Phe Trp Xaa Gly Arg Ser Arg Ala Ala
1               5                   10

<210> SEQ ID NO 183
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 4,6
<223> OTHER INFORMATION: Xaa=Citrulline

<400> SEQUENCE: 183

His Gln Lys Xaa Lys Xaa Gly Arg Ser Arg Ala Ala
1               5                   10

<210> SEQ ID NO 184
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6,10
<223> OTHER INFORMATION: Xaa=Citrulline

<400> SEQUENCE: 184

His Gln Lys Trp Arg Xaa Gly Arg Ser Xaa Ala Ala
1               5                   10

<210> SEQ ID NO 185
<211> LENGTH: 12
<212> TYPE: PRT
<213> ORGANISM: Artificial sequence
<220> FEATURE:
<223> OTHER INFORMATION: Derived from known cDNA sequences of human
      fillagrin
```

```
<220> FEATURE:
<221> NAME/KEY: VARIANT
<222> LOCATION: 6,10
<223> OTHER INFORMATION: Xaa=Citrulline

<400> SEQUENCE: 185

His Gln Ala Trp Arg Xaa Gly Arg Ser Xaa Ala Ala
1               5                   10

<210> SEQ ID NO 186
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 186

His Gln Asn Gln Trp Xaa Gly Arg Ser Arg Ala Ala
1               5                   10

<210> SEQ ID NO 187
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 187

His Gln Asn Ser Lys Xaa Gly Arg Ser Arg Ala Ala
1               5                   10

<210> SEQ ID NO 188
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 188

His Gln Lys Arg Arg Xaa Gly Arg Ser Arg Ala Ala
1               5                   10

<210> SEQ ID NO 189
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 189
```

His Gln Lys Arg Phe Xaa Gly Arg Ser Arg Ala Ala
1               5                   10

<210> SEQ ID NO 190
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 190

His Gln Lys Arg Tyr Xaa Gly Arg Ser Arg Ala Ala
1               5                   10

<210> SEQ ID NO 191
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 191

His Gln Lys Arg His Xaa Gly Arg Ser Arg Ala Ala
1               5                   10

<210> SEQ ID NO 192
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 192

His Gln Glu Arg Ala Xaa Gly Ser Ser Arg Ala Ala
1               5                   10

<210> SEQ ID NO 193
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 193

His Gln Glu Lys Met Xaa Gly Val Ser Arg Ala Ala
1               5                   10

<210> SEQ ID NO 194
<211> LENGTH: 12
<212> TYPE: PRT

<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 194

His Gln Lys Arg Gly Xaa Gly Trp Ser Arg Ala Ala
1               5                   10

<210> SEQ ID NO 195
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 195

His Gln Arg Arg Val Xaa Gly Trp Ser Arg Ala Ala
1               5                   10

<210> SEQ ID NO 196
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 196

His Gln Trp Asn Arg Xaa Gly Trp Ser Arg Ala Ala
1               5                   10

<210> SEQ ID NO 197
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 197

His Gln Gln Arg Met Xaa Gly Trp Ser Arg Ala Ala
1               5                   10

<210> SEQ ID NO 198
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6

<223> OTHER INFORMATION: Xaa=Citrulline

<400> SEQUENCE: 198

His Gln Ser His Arg Xaa Gly Trp Ser Arg Ala Ala
1               5                   10

<210> SEQ ID NO 199
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 199

His Gln Phe Arg Phe Xaa Gly Trp Ser Arg Ala Ala
1               5                   10

<210> SEQ ID NO 200
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 200

His Gln Lys Arg Arg Xaa Gly Trp Ser Arg Ala Ala
1               5                   10

<210> SEQ ID NO 201
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 6
<223> OTHER INFORMATION: Xaa=Citrulline

<400> SEQUENCE: 201

Gly Val Lys Gly His Xaa Gly Tyr Pro Gly Leu Asp
1               5                   10

<210> SEQ ID NO 202
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 4,5,7,8
<223> OTHER INFORMATION: Xaa=any amino acid but not cysteine or
      tryptophane
<220> FEATURE:
<221> NAME/KEY: VARIANT
<222> LOCATION: 6
<223> OTHER INFORMATION: Xaa=citrulline

```
<400> SEQUENCE: 202

His Gln Glu Xaa Xaa Xaa Xaa Xaa Ser Arg Ala Ala
1               5                   10

<210> SEQ ID NO 203
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,4,5,8
<223> OTHER INFORMATION: Xaa=any amino acid but not cysteine
<220> FEATURE:
<221> NAME/KEY: VARIANT
<222> LOCATION: 6
<223> OTHER INFORMATION: Xaa=citrulline

<400> SEQUENCE: 203

His Gln Xaa Xaa Xaa Xaa Gly Xaa Ser Arg Ala Ala
1               5                   10

<210> SEQ ID NO 204
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 3,4,5,8
<223> OTHER INFORMATION: Xaa=any amino acid but not cysteine
<220> FEATURE:
<221> NAME/KEY: VARIANT
<222> LOCATION: 6,10
<223> OTHER INFORMATION: Xaa=citrulline

<400> SEQUENCE: 204

His Gln Xaa Xaa Xaa Xaa Gly Xaa Ser Xaa Ala Ala
1               5                   10

<210> SEQ ID NO 205
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 4,5,7,8
<223> OTHER INFORMATION: Xaa=any amino acid but not cysteine
<220> FEATURE:
<221> NAME/KEY: VARIANT
<222> LOCATION: 6
<223> OTHER INFORMATION: Xaa=Citrulline

<400> SEQUENCE: 205

His Gln Glu Xaa Xaa Xaa Xaa Xaa Ser Arg Ala Ala
1               5                   10

<210> SEQ ID NO 206
<211> LENGTH: 12
<212> TYPE: PRT
<213> ORGANISM: Artificial sequence
<220> FEATURE:
<223> OTHER INFORMATION: Derived from known cDNA sequences of human
      fillagrin
```

```
<220> FEATURE:
<221> NAME/KEY: VARIANT
<222> LOCATION: 4,5,7,8
<223> OTHER INFORMATION: Xaa=any amino acid but not cysteine
<220> FEATURE:
<221> NAME/KEY: VARIANT
<222> LOCATION: 6,10
<223> OTHER INFORMATION: Xaa=citrulline

<400> SEQUENCE: 206

His Gln Glu Xaa Xaa Xaa Xaa Xaa Ser Xaa Ala Ala
1               5                   10

<210> SEQ ID NO 207
<211> LENGTH: 12
<212> TYPE: PRT
<213> ORGANISM: Artificial sequence
<220> FEATURE:
<223> OTHER INFORMATION: Derived from known cDNA sequences of human
      fillagrin
<220> FEATURE:
<221> NAME/KEY: VARIANT
<222> LOCATION: 1,2,3,4,5,6,8,9,10,11,12
<223> OTHER INFORMATION: Xaa=any amino acid but not cysteine
<220> FEATURE:
<221> NAME/KEY: VARIANT
<222> LOCATION: 7
<223> OTHER INFORMATION: Xaa=citrulline

<400> SEQUENCE: 207

Xaa Xaa Xaa Xaa Xaa Xaa Xaa Xaa Xaa Xaa Xaa Xaa
1               5                   10

<210> SEQ ID NO 208
<211> LENGTH: 4
<212> TYPE: PRT
<213> ORGANISM: Artificial Sequence
<220> FEATURE:
<223> OTHER INFORMATION: Derived from known cDNA sequences of human
      fillagrin

<400> SEQUENCE: 208

Ser Arg Ala Ala
1

<210> SEQ ID NO 209
<211> LENGTH: 4
<212> TYPE: PRT
<213> ORGANISM: Artificial Sequence
<220> FEATURE:
<223> OTHER INFORMATION: Derived from known cDNA sequences of human
      fillagrin
<220> FEATURE:
<221> NAME/KEY: VARIANT
<222> LOCATION: 2
<223> OTHER INFORMATION: Xaa=Citrulline

<400> SEQUENCE: 209

Ser Xaa Ala Ala
1

<210> SEQ ID NO 210
<211> LENGTH: 4
<212> TYPE: PRT
<213> ORGANISM: Artificial Sequence
<220> FEATURE:
<223> OTHER INFORMATION: Derived from known cDNA sequences of human
      fillagrin

<400> SEQUENCE: 210
```

```
Arg Pro Leu Asp
1

<210> SEQ ID NO 211
<211> LENGTH: 4
<212> TYPE: PRT
<213> ORGANISM: Artificial Sequence
<220> FEATURE:
<223> OTHER INFORMATION: Derived from known cDNA sequences of human
      fillagrin

<400> SEQUENCE: 211

Arg Val Val Glu
1

<210> SEQ ID NO 212
<211> LENGTH: 4
<212> TYPE: PRT
<213> ORGANISM: Artificial Sequence
<220> FEATURE:
<223> OTHER INFORMATION: Derived from known cDNA sequences of human
      fillagrin

<400> SEQUENCE: 212

Pro Gly Leu Asp
1
```